(12) United States Patent
Shushan et al.

(10) Patent No.: US 6,692,971 B2
(45) Date of Patent: Feb. 17, 2004

(54) METHOD OF ANALYZING DICARBOXYLIC ACIDS

(75) Inventors: Bori Shushan, Concord (CA); Mark Kushnir, Salt Lake City, UT (US); Gabor Komaromy-Hiller, Los Angeles, CA (US)

(73) Assignee: University of Utah Research Foundation, Salt Lake City, UT (US)

( * ) Notice: Subject to any disclaimer, the term of this patent is extended or adjusted under 35 U.S.C. 154(b) by 134 days.

(21) Appl. No.: 09/835,845

(22) Filed: Apr. 17, 2001

(65) Prior Publication Data

US 2002/0019056 A1 Feb. 14, 2002

Related U.S. Application Data

(60) Provisional application No. 60/197,910, filed on Apr. 17, 2000.

(51) Int. Cl.[7] .............................................. G01N 24/00
(52) U.S. Cl. ........................................ 436/173; 436/86
(58) Field of Search ................................... 436/86, 173

(56) References Cited

FOREIGN PATENT DOCUMENTS

JP          407291890 A   *  11/1995

OTHER PUBLICATIONS

Caruso et al. "Capillary GC–MS—stable isotope dilution analysis of methylmalonic acid in plasma: a candidate reference method for the diagnosis and the follow–up of methylmalonic acidemias", Chromatographia, 1993, v. 36, pp. 212–214.*

Magera et al. "Method for the Determination of Total Homocysteine in Plasma and Urine by Stable–Isotope Dilution and Electrospray Tandem Mass Spectrometry", Clin. Chem. (Washington, D. C.) (1999), 45(9), 1517–1522.*

Magera et al. "Methylmalonic acid measured in plasma and urine by stable–isotope dilution and electrospray tandem mass spectrometry", Clin. Chem. (Washington, D. C.) (2000), 46(11), 1804–1810.*

Bruins, et al. *Anal. Chem.* 2000; 72:3653–3659.

Chace DH, Millington DS, Terada N, Kahler, SG, Roe CR, Hofman LF, *Clin Chem* 1993 39:66–71.

Franke DR, Marsh DB, Nuttall KL *J Cap Elec* 1996; 3:125–129.

Giorgio AJ, Plaut GWE. *J Lab Clin Med* 1965; 66(4):667–676.

J. Cornbleet, N. Gochman, Clin. Chem., 25 (1979) 432.

Johnson DW, *Rapid Commun. Mass Spectrom.*, 1999, 13:2388–2393.

Marsh DB, Nuttall KL, *J Cap Elec* 1995; 2:63–67.

Montgomery JA, Mamer OA. *Methods Enzymol* 1988; 166:47–55.

Norman EJ, Berry HK, Denton MD. *Biomed Mass Spectrom* 1979; 6:546–552.

Parnet JM, Divry P, Vianey–Saban C, Mathieu M. *J Inher Metab Dis* 1996; 19:635–637.

(List continued on next page.)

*Primary Examiner*—Jill Warden
*Assistant Examiner*—Yelena Gakh
(74) *Attorney, Agent, or Firm*—Crowell & Moring, LLP

(57) ABSTRACT

A novel method for the qualitative and quantitative analysis of dicarboxylic acids in biological samples is provided. The method includes the steps of esterfying the acid component of the sample and subsequently analyzing the esterified sample using tandem mass spectroscopy using atmospheric pressure ionization techniques in the positive ion mode. The method is particularly useful in the determination of methylmalonic acid in biological samples, and thus, the diagnosis of vitamin $B_{12}$ deficiency.

29 Claims, 7 Drawing Sheets

OTHER PUBLICATIONS

Rifai N, Hagen T, Bradley L, Sakamoto M. *Ann Clin Biochem* 1998; 35:633–636.

Rinaldo P, Chiandetti L, Zacchello F, Daolio S, Traldi P. *Biomed Mass Spectrom* 1984; 11:643–646.

T. Niwa J. Chromatogr 1986; 379:313–45.

Westwood A, Taylor W, Davies G. *Ann Clin Biochem* 1979; 16:161–164.

Buchanan DN, Muenzer J, Thoene JG. *J Chromatogr* 1990; 534:1–11.

Frenkel EP, Kitchens RL. *J Clin Lab Med* 1975; 85:487–496.

Johnson AW, Mills K, Clayton PT. *Biochem Soc Trans* 1996; 24:932–938.

Kajita M, Niwa T, Watanebe K. *J Chromatogr Biomed Appl* 1993; 622:263–268.

Kushnir MM, Komaromy–Hiller G. *J ChromatogrB*, 2000; 741:231–41.

Matchar DB, Feussner JR, Millington DS, Wilkinson RH, Watson DJ, Gale D. *Ann Int Med* 1987; 106:707–710.

McCann MT, Thompson MM, Gueron IC, Lemieux B, Giguere R, Tuchman M. *Clin Chem* 1996; 42:910–914.

McGhie TK. *Cromatogr* 1991; 566:215–222.

Mikasa H, Sasaki K, Kodama H. *J Chromatogr* 1980; 190:501–503.

Millar KR, Lorentz PP. *J Chromatogr* 1974; 101:177–181.

Mills GA, Walker V, Clench MR, Parr VC. *Biomed Environ Mass Spectrom* 1988; 16:259–261.

Rashed MS, Ozand PT, Bucknall MP and Little D, *Pediatr. Res.*, 1995 38:324–331.

Rasmussen K. *Clin Chem* 1989; 35:260–264.

Stabler SP, Marcell PD, Podell ER, Allen RH, Lindenbaum J. *J Clin Invest* 1986; 77:1606–1612.

Straczek J, Felden F, Dousset B, Gueant JL, Belleville F. *J Chromatogr Biomed Appl* 1993; 620:1–7.

Young PB, Blanchflower WJ, Hewitt SA, Price J, Kennedy DG. *Analyst* 1995; 120:2199–2201.

Babidge PJ, Babidge WJ. *Anal Biochem* 1994; 216; 424–426.

Barness LA, Young D, Mellman WJ, Kahn SB, Williams WJ. *N Engl J Med* 1963; 268(3):144–146.

Bashir HV, Hinterberger H, Jones BP. *Br J Haematol* 1966; 12:704–711.

Burtis CA, Ashwood ER. Teits textbook of clinical chemistry. W.B. Saunders Company, Philadelphia, 1994, pp 2048–2049.

Coulombe JT, Shih VE, Levy HL. *Pediatrics* 1981; 67:26–31.

Cox EV, White AM, *Lancet* 1962; 853–856.

Fenton WA, Rosenberg LE. Disorders of Propionate and Methylmalonate Metabolism, in *The Metabolic and Molecular Bases of Inherited Disease*, (Scriver CR, Beaudet AL, Sly WS, Valle D. eds.), McGraw–Hill, Inc. New York, 1995, pp. 1423–1449.

Gibbs BF, Itiaba K, Mamer OA, Crawhall JC, Cooper BA. *Clin Chim Acta* 1972; 38:447–453.

Jakobs C, Sweetman L, Nyhan WL. *Clin Chim Acta* 1984; 140:157–166.

Lorentz PP, Gibb FM. *Lab Pract* 1974; 23:438.

Marcell PD, Stabler SP, Podell ER, Allen RH. *Anal Biochem* 1985; 150:58–66.

Nakamura E, Rosenberg LE, Tanaka K. *Clin Chim Acta* 1976; 68:127–140.

Norman EJ, Martelo OJ, Denton MD. *Blood* 1982; 59:1128–1131.

Schneede J, Ueland PM. *Anal Chem* 1995; 67:812–819.

Schneede J, Ueland PM. *Clin Chem* 1993; 39:392–399.

Stabler SP, Marcell PD, Podell ER and Allen RH; Lindenbaum J, J Clin Invest, 77(5): 1606–12 1986, May.

* cited by examiner

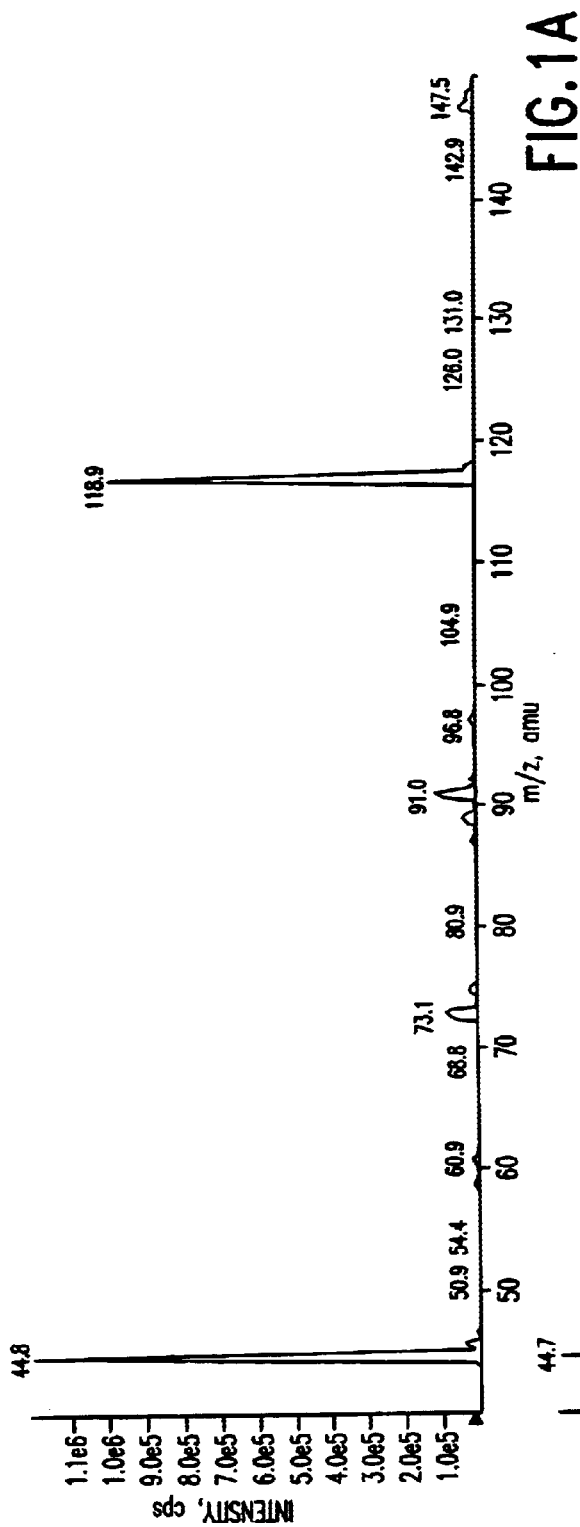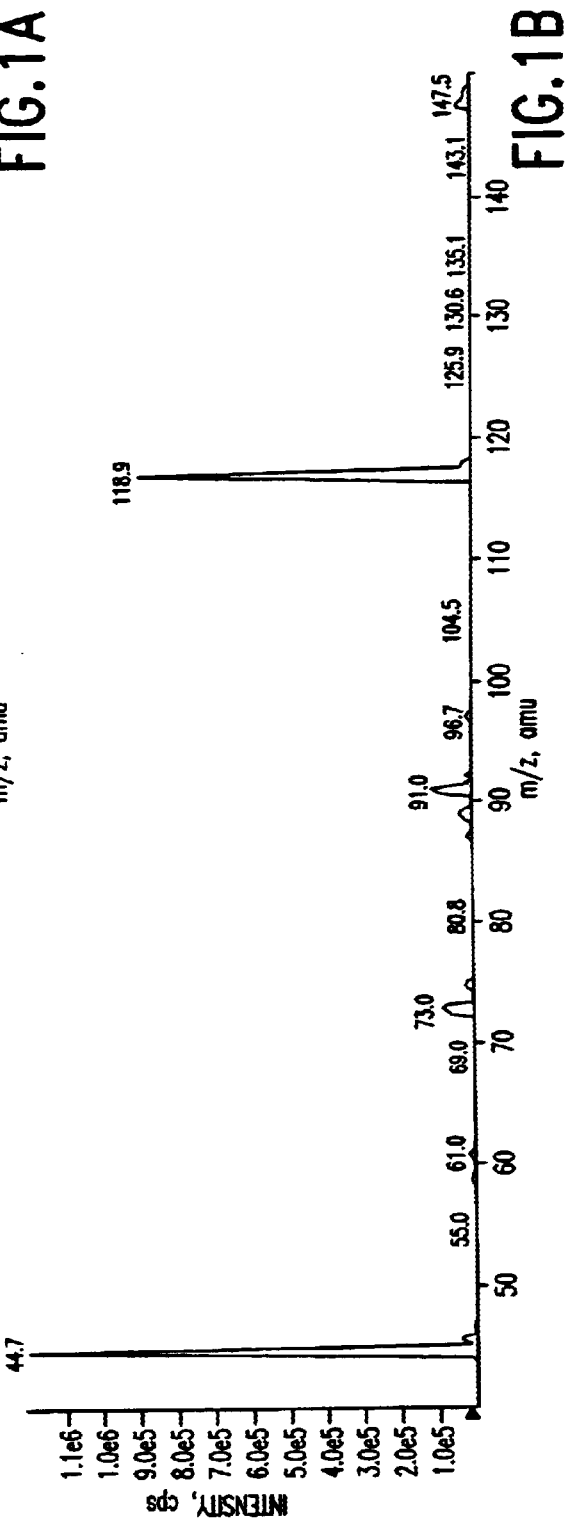

METHOD OF ANALYZING DICARBOXYLIC ACIDS

RELATED INVENTION

This application claims the benefit of U.S. Provisional Patent Application No. 60/197,910 filed Apr. 17, 2000.

FIELD OF THE INVENTION

The present invention relates to a method of selectively analyzing structural isomers of dicarboxylic acids based on the unique fragmentation of their derivatives using mass spectrometry (MS), and enhancement of selectivity for the analysis of the dicarboxylic acids through choice of the utilized derivative. In particular, the present invention relates to the determination of methylmalonic acid in a biological sample, and to the diagnosis of vitamin $B_{12}$ deficiency.

BACKGROUND OF THE INVENTION

Measurement of methylmalonic acid (MMA) became an important diagnostic procedure in clinical chemistry due to accumulated evidence that slightly increased concentrations of MMA was a marker of vitamin $B_{12}$ deficiency. MMA is a metabolic intermediate in the conversion of propionic acid to succinic acid (SA). Vitamin $B_{12}$ is an essential cofactor of the enzymatic carbon rearrangement of MMA to succinic acid and the lack of vitamin $B_{12}$ leads to elevated levels of MMA. Elevated levels of methylmalonic acid were found in the urine of vitamin $B_{12}$-deficient patients [1]. Deficiency of vitamin $B_{12}$ also causes serious and often irreversible neurological disorders named as subacute combined degeneration of the spinal cord [2]. A moderately elevated concentration of MMA (above 0.4 $\mu$mol/L in serum or plasma and above 3.6 mmol/mol CRT in urine) is an early indicator of vitamin $B_{12}$ deficiency. Frequency of positively tested samples with results consistent with vitamin $B_{12}$ deficiency is 1:20 to 1:50 depending on the population tested. Massive elevation of MMA in serum, plasma or urine (100 to 1000 fold above the concentrations characteristic for the vitamin $B_{12}$ deficiency) is consistent with methylmalonic acedemia, an inborn metabolic disorder. Frequency of the methylmalonic acedemia disorder in newborns is 1:20,000 [1,3].

Although, serum MMA and serum cobalamin measurements seem to have equal clinical sensitivity in detecting vitamin $B_{12}$ deficiency, there are advantages of measuring MMA instead of cobalamin. Firstly, serum or plasma vitamin $B_{12}$ levels may not reflect adequately tissue cobalamin status. Secondly, serum MMA level is 1000-fold greater than serum cobalamin level, and an elevation rather than decreased concentration is measured in vitamin $B_{12}$ deficiency. Thirdly, MMA is more stable than cobalamin.

Since the 1960s efforts have been directed towards developing a rapid, simple, sensitive, and specific analytical method for methylmalonic acid determination in biological fluids. In general, sample preparation is required which consists of MMA extraction step from a sample matrix, and, most of the time, a subsequent derivatization. To be able to detect vitamin $B_{12}$ deficiency the method is required to measure the low concentrations of MMA found in urine and serum (~1 $\mu$mol/L in urine, ~0.1 $\mu$mol/L in serum). The derivatization step is necessary to improve MMA detection by UV or fluorescent detector [4–10], or to convert the organic acid to a volatile derivative for GC separation [11–30].

Solvent [7,10,12,18–20,22–27,33–36,38,39] and solid-phase extractions [9,11,16,28,29,31,37], preparative chromatography [7,13] or solvent extraction and HPLC (combined) [14,17] have been used to separate MMA from biological samples prior to an instrumental analysis. For serum specimens, a protein precipitation step precedes the extraction. For solvent extraction, the preferred solvents have been diethyl ether, ethylacetate, or both. High MMA recovery was required otherwise the analytical method was not sensitive enough to detect MMA. Some authors used multiple extraction and combined the extracts [10,12,19,20, 22–24,34–36], while others utilized saturated NaCl to increase ionic strength of the solution [19,20,22–25,34]. In some cases the extracts were dried with $MgSO_4$ or $Na_2SO_4$ in order to eliminate residual water for the subsequent derivatization for GC analysis [10,12,14,20]. Generally, tedious extraction was required to reduce possible interferences and to obtain an extract that was suitable for further analysis.

There are some methods described in the literature which do not include an extraction step [4–6,8]. Among these are paper [4] and thin-layer chromatography [6,8], colorimetry [5], GC-MS [15], and LC-MS [31,32]. Paper and thin-layer chromatography were used only as qualitative screening methods [4,6,8], and positive specimens were subjected to the more specific and quantitative GC or GC-MS analysis [8]. Norman et al. [15] did not use extraction for urine dicarboxylic acid determination. After addition of the internal standard solution, the sample was evaporated to dryness and derivatized for subsequent GC analysis. This method can be used to identify inborn errors of metabolism from urine samples only and cannot be applied to serum specimens because of their high protein content. The two LC-MS based methods [31,32] were developed for urine organic acid analysis in inborn errors of metabolism screening, and were not optimal for determination of even mildly elevated concentrations of MMA. The authors were able to see methylmalonic acid only at very elevated levels. Instrumental analysis time, using any of the methods described above, range from 10–60 minutes per sample. Furthermore, these methods were only suitable to identify patients with methylmalonic acedemia and were not sensitive enough for the vitamin $B_{12}$ deficiency screening.

Derivatization schemes that have been used in methods of determining MMA are method dependent In TLC, HPLC, or CE, derivatization of MMA is required for detection purposes. In GC methods, derivatization is required to convert MMA to a volatile derivative. There are few published methods where analysis of MMA did not require derivatization [31,32,34–39]. Mills et al. [31], Buchanan et al, [32], Kajita et al. [37] have used LC-MS to analyze organic acids in urine specimens No derivatization was needed, however, none of these methods were sensitive enough to analyze MMA in normal urine specimens. Frenkel et al. [34] describe a GC method for urinary MMA determination without derivatization of MMA. MMA from urine specimens was extracted and directly injected into a GC. At the injection port temperature of 225° C. MMA decomposed to propionic acid, and was analyzed as such. This result gave the sum of propionic and methylmalonic acid in the specimen. From a second injection with a lower injection port temperature, propionic acid alone was determined. Concentration of MMA was calculated as the difference between the two measurements. Mikasa et al. [35] describe an isotachophoresis method for urine MMA determination which included an extraction but no derivatization step. Although the detection limit using this method was 0.4 $\mu$mol/L MMA in urine samples, it was achieved by extracting 10 mL of urine. This method is clearly not practical and sensitive enough for serum specimens. Rinaldo et al. [36] describe a CAD MIKES (collisionally activated decomposition mass analyzed kinetic energy spectrometry) technique which has been used to identify patients with methylmalonic acedemia. The technique is not quantitative and by no means is sensitive enough to measure normal concentrations of MMA in urine or serum. Nuttall et al. [38,39] reported a capillary electrophoresis method for MMA determination in urine [38] and serum [39]. To avoid derivatization, they used indirect UV detection; however, using this method, sensitivity was limited and there was no specificity. All the above methods were designed to diagnose organic acedemias in urine specimens. Accordingly, none have adequate sensitivity to measure MMA in serum samples for diagnosis of vitamin $B_{12}$ deficiency.

The work by Allen et. al [40] on MMA and SA analysis by GC/MS showed that the t-butylsilyl ester derivatives of the compounds gave nearly identical mass spectra showing analytically useful fragment ions at m/z 331 and 289 MMA and SA were analyzed by GC/MS using SIM of the common 289 fragment ion requiring that MMA and SA be chromatographically separated prior to MS detection. The method has sufficient sensitivity and performance characteristics to allow determination of both vitamin $B_{12}$ deficiency and methylmalonic acedemia. The disadvantages associated With this GC/MS method is the requirement for time- and resource-consuming sample preparation as well as a relatively low throughput (3–6 samples per hour).

Recent work by Johnson [41] involves the determination of long- and very-long chain fatty acids by Ionspray (nebulizer assisted electrospray) MS—MS. The fatty acids are derivatized to form dimethylaminoethyl (DMAE) esters via a 2-step condensation reaction using oxalyl chloride and dimethylaminoethanol as reagents. The analogous reaction is the use of acylchloride and butanol (which acts like butanolic hydrochloride) to form butyl esters of amino acids and acylcarnitines [42]. The DMAE esters are ionized in the positive ion mode and fragment to form a 45 u neutral loss (dimethyl amine) and strong characteristic product ions of m/z 72 and 90. This allows for several ways of screening for a wide variety of acids using neutral loss and precursor ion MS—MS scans. The reagent produces a strongly basic derivative which would very much enhance the response of these acids in the positive ion mode. This reagent should work for MMA and SA; however, the specificity for the selective ionization of dicarboxylic acid butyl esters over other acids would likely be lost since all the acids present in a sample would be derivatized and the amino group on the DMAE moiety would readily protonate. In other words, DMAE esters of all acids, regardless of their structure, would ionize equally well. Furthermore, the fragmentation of DMAE ester derivatives is dominated by fragmentation reactions described above and would likely not lead to a dramatic difference in fragmentation between the isobaric acids MMA and SA.

Work by Chace, et. al. [42] demonstrated the FIA (Flow Injection Analysis)-MS—MS analysis of amino acids as n-butylated ester derivatives. This included the amino acids Glu and Asp which have two carboxylic acid moieties. In their work, the purpose of the derivatization was to force cationic character upon these amino acids as well as eliminate interferences from other endogenous analytes which do not undergo the neutral loss of 102 MS—MS transition characteristic of amino acids. Isomeric amino acids still interfere with one another. Once derivatized the remaining amino group is readily protonated under eleviated pH and IonSpray [43]. The method was shown only to be effective for the analysis of amino acids and acylcarnitines with no reference to the analysis of dicarboxylic acids such as MMA.

Even though esterification of acidic analytes is commonly used for GC/MS analysis there is no reference to the use of such derivatives for the selective LC/MS analysis of dicarboxylic acids and for MMA and SA in particular. The purpose of esterification of MMA for GC/MS analysis is to render the molecule sufficiently nonpolar to be amenable to GC. Since the GC/MS spectra of MMA and SA esters are nearly identical [40], GC separation of these isobaric analytes is required prior to MS analysis. For LC/MS applications employing API (atmospheric pressure ionization) techniques like Ionspray, organic acid esterification would be counterintuitive because the nonpolar derivative in solution would be less likely to be ionized than its underivatized form.

The major obstacle for MMA analysis in biological fluids is potential interference by low molecular weight organic acids, and especially from the naturally occurring structurally related isomer, succinic acid. Chromatographic characteristics and mass spectra of succinic acid are almost identical to that of MMA and because succinic acid is a product of MMA degradation and is usually present in samples at a greater concentration than MMA, succinic acid interference is difficult to overcome. There is a need, thus, for a method of determining MMA in biological samples in order that vitamin $B_{12}$ deficiency and methylmalonic acedemia can effectively be diagnosed without interference from succinic acid.

SUMMARY OF THE INVENTION

Accordingly, the present invention provides a method for determining the presence of a dicarboxylic acid in a sample comprising the steps of:

extracting the acidic component from the sample;

derivatizing the acidic component; and using mass spectromety and atmospheric pressure ionization in the positive ion mode to determine the presence of a dicarboxylic acid of interest.

In another aspect, the present invention provides a method for determining the presence and quantity of methylmalonic acid in a sample comprising the steps of 1) extracting the acidic component of the sample;

2) derivatizing the acidic component; and 3) determining the presence of methylmalonic acid using mass spectrometry and atmospheric pressure ionization in the positive ion mode.

In another aspect of the present invention, there is provided a method for diagnosing vitamin $B_{12}$ deficiency in a patient comprising the steps of:

1 ) obtaining a biological sample from the patient;

2) extracting the acidic component from the sample;

3) derivatizing the acidic component;

4) analyzing the sample by mass spectrometry employing atmospheric pressure ionization in the positive ion mode; and 4) determining the presence of methylmalonic acid at a concentration of at least 0.4 $\mu$mol/L in the sample.

The present invention advantageously provides a mass spectrometry method having a specificity toward the detection of dicarboxylic acids present in a sample, since all other acids present in the sample that do not have a dicarboxylic acid moiety are undetectable under the conditions of this method. The detection of dicarboxylic acids is accomplished by exploiting the unique ionization of derivatized dicarboxylic acids that occurs in the positive ion mode of an atmospheric pressure ionization (API) ion source such as IonSpray or electrospray. The method also provides a means for distinguishing between isobaric dicarboxylic acids, such as methylmalonic acid (MMA) and succinic acid (SA), by exploiting the unique collisionally induced decomposition (CID) fragmentation thereof that occurs when molecular ions of derivatized MMA and SA undergo upfront (in source) CID in single MS, or CID in a tandem mass spectrometer. As a result, the necessity for an initial separation step, to separate such isobaric components, can be eliminated thereby simplifying sample analysis and significantly reducing analysis time.

These and other aspects of the present invention will be described in detail by reference to the following figures in which:

BRIEF DESCRIPTION OF THE DRAWINGS

FIG. 1 is the product ion mass spectra of succinic (A) and methylmalonic (B) acids in the negative ion mode;

DETAILED DESCRIPTION OF THE INVENTION

Figure 2:
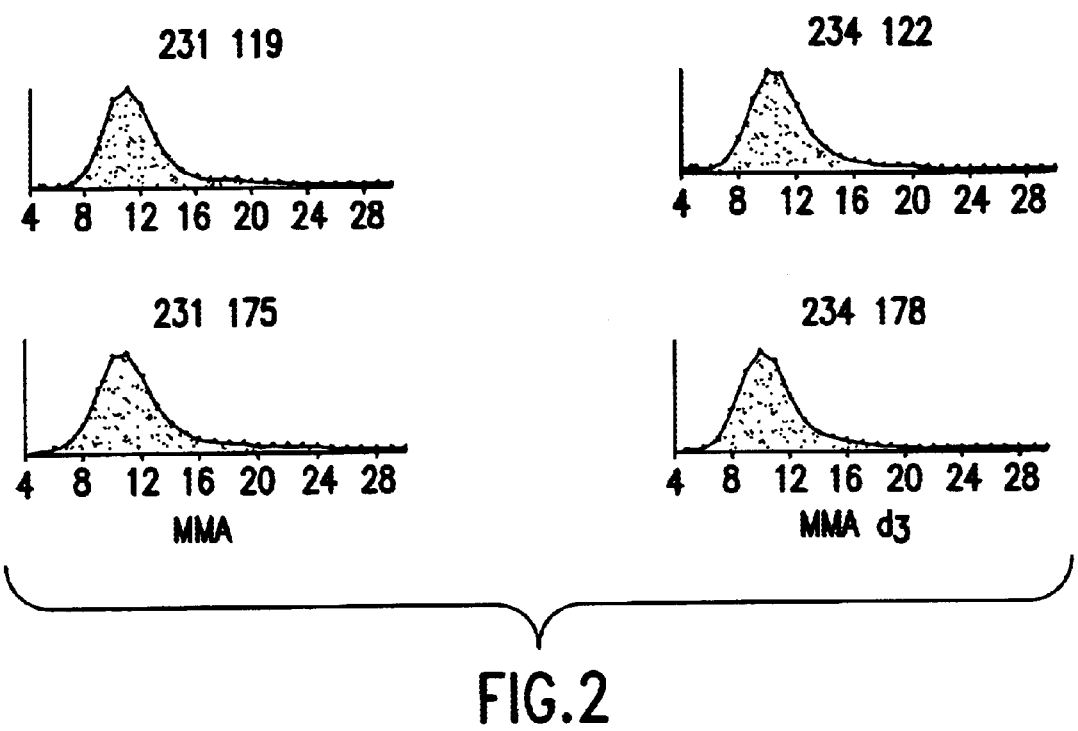
FIG. 2 is the multiple reaction monitoring chromatograms of extracted plasma control containing 0.4 μmol/L of MMA and 1.5 μmol/L of MMA $d_3$ internal standard

A method for the qualitative and quantitative analysis of dicarboxylic adds in a sample using mass spectrometry (MS) is provided in which the acidic component of the sample is extracted, derivatized and then the presence and quantity of the dicarboxylic acid of interest is determined by MS using atmospheric pressure ionization (API) techniques in the positive ion mode.

The present method is not limited with respect to the dicarboxylic acids that it may be used to analyze. Specifically, there is no restriction as to the position of the carboxyl group in the dicarboxylic acid, for example, the number of methylene groups between the carboxyl groups, nor is there any restriction as to the presence of other functional groups in the dicarboxylic acid. Examples of dicarboxylic acids that may be analyzed using the present method include saturated dicarboxylic acids such as succinic acid, adipic acid, suberic acid, sebacic acid, dodecanoic acid, pimelic acid, azelaic acid, dodecandioic acid, tetradecanoic acid, hexadecanoic acid, and octadecanoic acid; unsaturated dicarboxylic acids such as heptanedioic acid, 2-octainedioic acid, 4-octenedioic acid, 2-decenedioic acid, 3-decenedioic acid, 4-decenedioic acid, 5-decenedioic acid, 3-dodecanoic acid, 5-dodecanoic acid, 5-tetradecanoic acid, tetradecadienedioic acid, hexadecenedioic acid, octadecenedioic acid, and octadecadienedioic acid; branched dicarboxylic acids such as methylmalonic acid, ethylmalonic acid and methylsuccinic acid; and hydroxy dicarboxylic acids such as 2-hydroxyglutaric acid and 3hydroxyglutaric acid. The method is particularly useful for the determination of methylmalonic acid in the presence of other organic acids.

The present method includes an extraction step in which the acidic component is extracted from the sample matrix prior to the MS analysis. The term "acidic component" as it is used herein with respect to the sample to be analyzed is defined as the portion of the sample containing acidic or "proton-donating" compounds such as, for example, organic acids including carboxylic acids (monocarboxylic and polycarboxylic), short chain aliphatic acids, long chain aliphatic acids, monohydroxy aliphatic acids, polyhydroxy aliphatic acids, ketoacids, aromatic acids, conjugates of acids, and inorganic acids. The extraction may be conducted in a number of conventional ways. For example, the extraction may be of the solid phase type in which the acidic component of the sample is adsorbed onto a solid phase and then eluted from the adsorbent. Suitable solid phases for use in extracting the acidic component from a sample include anion exchange adsorbents. Solid phase microextraction may also be used in which the acidic component is adsorbed onto an appropriate fiber, derivatized and then eluted. Alteratively, the extraction step may be a liquid—liquid extraction in which the acidic component is partitioned in an organic solvent which is then removed from the remainder of the sample. Briefly, the liquid—liquid extraction step involves admixture of the sample with an extraction solvent, such as methyl tert-butyl ether (MTBE), containing a small amount of an acid, for example, 3% of phosphoric acid The sample is then vortexed and centrifuged, and the organic phase is retained for analysis.

Prior to proceeding with the MS analysis, the sample is derivatized in order to esterify the extracted acidic component of the sample, and specifically, to esterify the dicarboxylic acids present in the sample. There is no particular limitation with respect to the type of ester derivative suitable for use in the present method. The most suitable ester derivative will be the ester that allows efficient determination of the dicarboxylic acid of interest and, more specifically, allows for differentiation of the dicarboxylic acid of interest in the presence of potentially interfering compounds, particularly isobaric components, if they exist Thus, dialkyl esters, including both straight and branched chain alkyl groups, are suitable for use to esterify the acidic component according to the present method. Examples of suitable alkyl groups include for example methyl, ethyl, n-propyl, isopropyl, n-butyl and n-amyl groups. Unsaturated alkyl groups, including both alkenyl and alkynyl groups, are also suitable for use. Preferred esters for use include those esters which result in stable protonated molecular ions or adducts, having an MS response significantly greater than the background noise, demonstrate enhanced ionization efficiency and lead to more unique fragmentation compared to the potentially interfering compounds. The production of stable molecular ions is an important factor which imparts a specificity towards dicarboxylic acids when using the present method. The method renders acids having fewer than 2 carboxylate moieties transparent to MS detection since the alkyl esters of such acids do not produce stable molecular ions efficiently in the positive ion mode. In this regard, alkyl esters having at least one carbon atom between the carboxyl groups of the dicarboxylic acid exhibit both enhanced ionization efficiency and result in more stable molecular ions. Accordingly, n-propyl, n-butyl, and n-amyl esters are examples of preferred esters, for the determination of dicarboxylic acids in general, and particularly for the determination of methylmalonic acid. In a preferred embodiment of the present invention, the n-butyl ester is particularly well suited to the determination of methylmalonic acid in biological samples in accordance with the present invention.

Derivatization of the acidic component of a sample to form esters, and in particular, to form esters of the dicarboxylic acids in the sample, is conducted using conventional methodology. For example, dicarboxylic acids can be esterified by reaction with an alcohol comprising the substituent R group of choice in an acidic environment. Alternatively, esterfcation of the dicarboxylic acid can also be accomplished by conversion first to an acid chloride, followed by reaction with the appropriate R-containing alcohol Following derivatization, the sample may optionally be filtered prior to MS analysis to further clean the sample. Such filtration may be accomplished by methods well-known in the art. The use of an in-line filter, guard column or liquid chromatography are each suitable for the filtration of the sample prior to MS analysis In some instances, means to filter the sample is incorporated in the MS instrumentation, operating as, for example, an LC-MS system. This filtration step does not necessarily function to chromatographically separate analytes in the sample, but merely to remove undesirable components in the sample, such as salts, just prior to MS analysis.

The esterified sample is then subjected to MS analysis. The present MS method utilizes atmospheric pressure ionization (API) techniques in the positive ion mode to ionize esterified dicarboxylic acids. API techniques include electrospray ionization (ESI), nebulizer assisted electrospray (also known as IonSpray), APCI-heated nebulizer and atmospheric pressure photoionization (APPI) [44]. In API techniques such as ESI or IonSpray, analytes of interest exist as charged species in the mobile phase, for example, protonated or ammoniated molecular ions. During the ionization process these molecular ions are desorbed into the gas phase at atmospheric pressure. The molecular ions are then focused into the MS analyzer for analysis and detection. These methods of ionization advantageously provide a specificity not attainable in the negative ion mode. Molecular ions formed in the positive ion mode allow identification of dicarboxylic acids while excluding detection of other classes of organic acids, the alkyl esters of which are not proton affinate enough to exist in ionic form in the positive ion mode.

The present dicarboxylic acid analytes can also be detected as ionic adducts formed when coupled with an ionic modifier or buffer. Examples of ionic modifiers suitable for this purpose include formic acid, acetic acid, ammonium acetate, ammonium formate, ammonium bicarbonate, triethylamine, trimethylamine, puridine and substituted puridines. The stability of these adducts is related to the polarity of the analyte molecule. Generally, the more oxygen atoms incorporated into the derivatized carboxylic acid analyte, the higher the polarity and the stronger the ionic analyte-modifier complex. Thus, esterified dicarboxylic acids form more stable ions than esterified monocarboxylic acids and the former is observed with much better sensitivity than the latter. In fact, under the conditions used in the present method, only the protonated and adducted (e.g. ammoniated) molecular ions of the esterified dicarboxylic acids are observed.

The MS analysis may be conducted with a single mass analyzer (MS), a "tandem-in-space" mass analyzer such as a "triple quadrupole" tandem mass spectrometer (MS—MS) and "tandem-in-time" mass analyzer such as a Paul ion trap or Fourier Transform Ion Cyclotron Resonance (FT-ICR) which are often referred to as $MS^n$, provided that the $MS^n$ systems are utilized in conjunction with API techniques in the positive ion mode as set out above. In a single mass analyzer, the ionized sample undergoes "upfront" collisionally induced dissociation (CID) between the atmosphere-to-vacuum interface and the mass analyzer. Product ions related to the analyte(s) of interest and unfragmented analyte ions are passed through the mass filter for analysis and detection. Since only a single mass analyzer is used the selectivity and specificity of this technique is limited. Using MSMS, the first mass filter selects the molecular ion of the esterified dicarboxylic acid of interest while the second mass filter selects specified product or fragment ions. Between these stages of mass filtration, the precursor molecular ions selected by the first stage undergo collisionally induced dissociation (CID) to produce product or fragment ions. The particular molecular and fragment ions of interest will, of course, vary with the structure of the target analyte of interest. The final stage of mass filtration selects only the fragment ions which are related and specific to the analytes of interest. This tandem MS analysis provides a means to differentiate between dicarboxylic acids not previously distinguishable due to differences in the CID fragmentation of certain derivatized forms of these acids as detected by the second stage of mass analysis. This is particularly desirable in the analysis of biological samples containing isobaric components as described below. In $MS^n$ techniques, molecular ions are also isolated from other ions prior to fragmentation into representative productions. The difference between this and the other mass analyzers described above is that the isolation, fragmentation and subsequent analysis steps take place sequentially in time, each process finishing before the next begins. The process can be repeated any number of times where the product ions formed from a molecular ion in turn become the precursor ion for subsequent CID and formation of the next generation product ions. This process can be summarized in the following expression:

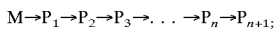

$$M \rightarrow P_1 \rightarrow P_2 \rightarrow P_3 \rightarrow \ldots \rightarrow P_n \rightarrow P_{n+1};$$

where each "→" represents mass separation followed by a CID step. The production of $P_1$ is MS—MS because it has 2 mass separation steps, the production of $P_2$ is $MS^3$ because it has 3 mass separation steps, and so on until the production of $P_{n+1}$ is $MS^n$ because it has "n" mass separation steps. The $MS^n$ process has the potential for very high specificity.

Of particular interest is the diagnostic application of the present method to accurately determine levels of specific dicarboxylic acids in biological samples, such as serum, plasma, saliva and urine, which are indicative of disease. The specificity of the present method allows for not only a qualitative determination of a dicarboxylic acid of interest, but also an accurate quantitative determination when compared against appropriate standards. As will be appreciated, accurate quantitative determination is important in the diagnosis or monitoring the status of a disease state.

In one embodiment of the invention, the method is useful to determine the level of methylmalonic acid in a biological sample, moderately elevated levels of which, for example, levels greater than about 0.4 μmol/L, are indicative of vitamin $B_{12}$ deficiency, while greater levels of methylmalonic acid are indicative of methylmalonic acedemia. In order to accurately reflect levels of MMA of about 0.4 μmol/L, the method used to diagnose vitamin $B_{12}$ deficiency should be able to detect levels of MMA at least as low as 0.2 μmol/L. Accordingly, using the present method, the acidic component of a biological sample is extracted, n-butyl esterified and analyzed by MS—MS. The MS—MS response of the n-butyl ester of methylmalonic acid includes either a protonated or ammoniated precursor molecular ion having a mass-to-charge ratio (m/z) of 231 or 248, respectively, and characterizing product ions having an m/z of 119 and 175 (see FIGS. 3 and 4). Quantitative analysis of methylmalonic acid is based either on the MS—MS transitions 231→119 or 231→175 for the protonated molecular ion, or the MS—MS transitions 248→119 or 248→175 for the ammoniated molecular ion relative to that of the deuterated MMA internal standard. The qualitative analysis is based on the ratio of the transitions identified above for the protonated or ammoniated molecular ions. In this regard, lack of interference with the internal standard $d_3$ MMA can be confirmed based on the ratio of the MS—MS transition (m/z) 234→178 to 234→122. In a preferred embodiment of the present invention, qualitative analysis of MMA is based on the relative ratio of MS—MS transition m/z 231→175 to the transition of 231→119 for the protonated molecular ion or on the relative ratio of MS—MS transition 248→175 to the transition of 248→119 for the ammoniated molecular ion, and its quantitative analysis is based on the MS—MS transition 231→119 or 248→119 for the protonated and ammoniated molecular ions, respectively, relative to the MS—MS transitions for the deuterated MMA internal standard 234→122 or 251→122, respectively.

The present method advantageously allows differentiation between methylmalonic acid and its isobaric component, succinic acid, which generally coexist in biological samples. This is due to the unique fragmentation pattern of di-n-butyl methylmalonic acid. This is evident in the MS—MS analysis described in the specific examples and illustrated in FIGS. 3 and 4. In contrast to MS—MS analysis of methylmalonic acid, the m/z 231 protonated or the m/z 248 ammoniated molecular ions of the di-n-butyl ester of succinic acid do not produce significant signals for the fragment ions having m/z of 119 and 175. As one of skill in the art will appreciate, charge transfer reagents and/or adduct-forming modifiers other than ammonium formate may be used to produce molecular ions of MMA and SA that similarly allow differentiation of these compounds.

The present method may also be used to diagnose dicarboxylic acedemia, another pathological condition that leads to abnormal concentrations of dicarboxylic acids in biological fluids of affected patients Increased excretion of dicarboxylic acids has been described in a number of diseases. These include congenital lactic acidosis, glycogen storage disease types I and II, systemic carnitine deficiency, glutaric acedemia type II, Jamaican vomiting sickness, hyperglycemea, Rye's syndrome, non-ketoic dicarboxylic acedimia, ethylmalonicadipic acedemia. Examples of dicarboxylic acids detected in elevated concentration in the urine of patients with different forms of dicarboxylic acedemia include saturated dicarboxylic acids such as glutaric acid, adipic acid, pimelic acid, suberic acid, azelaic acid, sebacic acid, dodecandioic acid, tetradecanoic acid, hexadecanoic acid, and octadecanoic acid; unsaturated dicarboxylic acids such as heptanedioic acid, 2-octainedioic acid, 4-octenedioic acid, 2-decenedioic acid, 3-decenedioic acid, 4-decenedioic acid, 5-decenedioic acid, 3-dodecanoic acid, 5-dodecanoic acid, 5-tetradecanoic acid, tetradecadienedioic acid, hexadecenedioic acid, octadecenedioic acid, and octadecadienedioic acid; branched dicarboxylic acids such as methylmalonic acid, ethylmalonic acid and methylsuccinic acid; and hydroxy dicarboxylic acids such as 2-hydroxyglutaric acid and 3-hydroxyglutaric acid [45].

Embodiments of the present invention will be described by reference to the following specific examples which are not to be construed as limiting.

EXAMPLE 1

Comparison of Monocarboxylic Acid and Dicarboxylic Acid Detection Using Positive Ion Mode MS—MS Several monocarboxylic acid esters with different additional functional groups were evaluated using MS—MS. The n-butyl esters were prepared as follows. 40 uL of stock standard of the acids (0.01 μmol/L) were aliquoted into new tubes. The solvent was evaporated and the residues reconstituted with 40 uL of n-butanol containing 3N HCl. The tubes were incubated at 60° C. for 15 minutes. Excess derivatizing reagent was evaporated and the remaining residues were reconstituted with 4 mL of methanol containing 5% of 0.005M $NH_4$ formate. The expected molecular weights (MW), and $[MH]^+$ and $[M+NH_4]^+$ molecular ions for the n-butyl ester derivatives are presented in the Table 1. The MS—MS conditions of the experiment were as follows: Positive ion mode; Q1 and Q3 optimized for MMA di-n-butyl derivative; all acids were at a concentration of ca. 10,000 ng/mL in 95% methanol and 5% $NH_4$ formate buffer. Injection of each sample was by syringe infusion at a flow rate of 5 L/min into the IonSpray ion source.

TABLE 1

Expected molecular ions (m/z) for representative mononocarboxylic acids

| | Acid | | | |
|---|---|---|---|---|
| Molecular ion | 2-OH-3-methylvaleric | 2-OH-isovaleric | 2-oxyisovaleric | 2-hydroxy-butyric |
| Underivatized MW | 132 | 118 | 116 | 104 |
| n-Butyl ester [MH]+ | 189 | 175 | 173 | 161 |
| n-Butyl ester [M + NH4]+ | 206 | 192 | 190 | 178 |

The molecular ions $[MH]^+$ and $[M+NH_4]^+$ for all the representative monocarboxylic acid esters were either not present or were comparable in size with the background noise, and thus were invisible, as compared to the molecular ions of the dicarboxylic acids.

The relative ionization efficiency and fragmentation pattern for butyl esters of dicarboxylic acids with different numbers of —$CH_2$— groups was evaluated using MMA, 2—OH-glutaric, adipic, suberic, sebacic and dodecanoic acids. Sample preparation and MS—MS conditions were the same as utilized for the analysis of monocarboxylic acids. The molecular ions, and M+1 and M+17 mass ion fragments for the dicarboxylic acid derivatives are presented in the Table 2.

TABLE 2

Expected molecular ions (m/z) for the dicarboxylic acid derivatives.

| | Acid | | | | | |
|---|---|---|---|---|---|---|
| Molecular ion | MMA | 2-OH-glutaric | Adipic | Suberic | Sebacic | Dodecanoic |
| Underivatized MW | 118 | 148 | 146 | 174 | 202 | 230 |
| n-Bu ester [MH]+ | 231 | 261 | 259 | 287 | 315 | 343 |
| n-Bu ester [M + NH4]+ | 248 | 278 | 276 | 304 | 332 | 360 |

Absolute abundance of the $[MH]^+$ and $[M+NH_4]^+$ molecular and fragment ions of the dicarboxylic acids are presented in the Table 3.

TABLE 3

Absolute response (cps) of the [MH]$^+$ and [M + NH$_4$]$^+$ molecular and fragment ions of the dicarboxylic acids di-n-butyl esters.

| Derivative | Q1 [MH]$^+$ ion abundance | Q1 [M + NH$_4$]$^+$ ion abundance | MS-MS product of [MH]$^+$, (loss of m/z 130) |
|---|---|---|---|
| MMA* | 2.90E+07 | 1.00E+07 | 9E6 (loss of m/z 112) |
| 2-OH-glutaric | 2.20E+07 | 1.30E+07 | 1.2E7 |
| Adipic | 1.60E+07 | 9.00E+06 | 7E6 |
| Suberic | 1.15E+07 | 1.45E+07 | 6E6 |
| Sebacic | 1.35E+07 | 1.75E+07 | 7E8 |
| Dodecanoic | 1.55E+07 | 1.60E+07 | 7E6 |

*Only MMA showed the neutral loss of m/z 112 in the MS-MS mode. The rest of the compounds showed a preferred neutral loss of m/z 130 similar to succinic acid (SA).

These above combined results suggest that: 1) all the esterified dicarboxylic acids produce [MH]$^+$ and [M+NH$_4$]$^+$ molecular ions; 2) the number of —CH$_2$— between the carboxyl groups does not affect the n-butyl ester ability to produce stable positively charged molecular ions nor decrease the molecular ion abundance; 3) MS—MS fragment ions m/z 175 and 119 (loss of m/z 56 and 112) in n-butyl-MMA are unique compared to the other evaluated dicarboxyilic acid derivatives; 4) for all the other acid esters (including succinic acid) the major product ions are loss of m/z 74 and 130; 5) the method works for dicarboxylic acids with additional functional groups present within the structure (e.g. 2OH-glutaric acid); and 6) derivatized monocarboxylic acids do not produce stable [MH]$^+$ and [M+NH$_4$]$^+$ molecular ions.

EXAMPLE 2

Analysis of MMA and Succinic Acid

MMA and succinic acid samples were prepared as Follows. An internal standard (MMA d$_3$) and extraction solvent containing 3% phosphoric acid were added to the tubes containing aliquots of standards, controls and patient samples, and then the tubes were vortexed and centrifuged. The organic phase of each was then transferred to new tubes. The solvent was evaporated, and the remaining residue was derivatized with 3N HCl in n-butanol to obtain di-butyl-MMA ester. Excess derivatizing reagent was evaporated and the residue reconstituted with the mobile phase. Sample aliquots were transferred into autosampler vials, and injected into the LC-MS—MS (triple quadrupole mass spectrometer using TurboIonSpray ion source, e.g. the API 2000 by PE SCIEX).

Extracted plasma control containing 0.4 μmol/L of MMA and 1.6 μmol/L of MMA d$_3$ internal standard were prepared as described above, MRM (multiple reaction monitoring) chromatograms of each are shown in FIG. 2.

The total run time was ca. 60 sec with the maximum MMA eluting at ca.17 sec. The ions (m/z) 231 and 234 are selected by Q1 for the MS—MS fragmentation reactions (m/z) 231→119, 231→175, and 234→122, 234→178. The ratio of the integrated peak response for MMA (231→119) vs. MMA d$_3$ (234→122) is used to calculate the concentration of MMA. The other MS—MS transitions are used for qualitative confirmation purposes to assure correct qualitative identification of MMA (absence of interference from co-extracted sample constituents such as SA). One of the key features of the present LC-MS—MS method is the ability of the analyzer to differentiate MMA from its major endogenous potential interference, SA. SA is the final product of the metabolic conversion of propionic acid and under normal conditions may be present in 10 to 100 fold greater concentration compared to MMA. A method not distinguishing MMA from SA would be of no clinical value, Fortuitously, the 231→119 and 231→175 fragmentation pathways are 100 and 30 times, respectively, more abundant for MMA than for SA (see Table 4 below and FIG. 3).

Figure 5A:
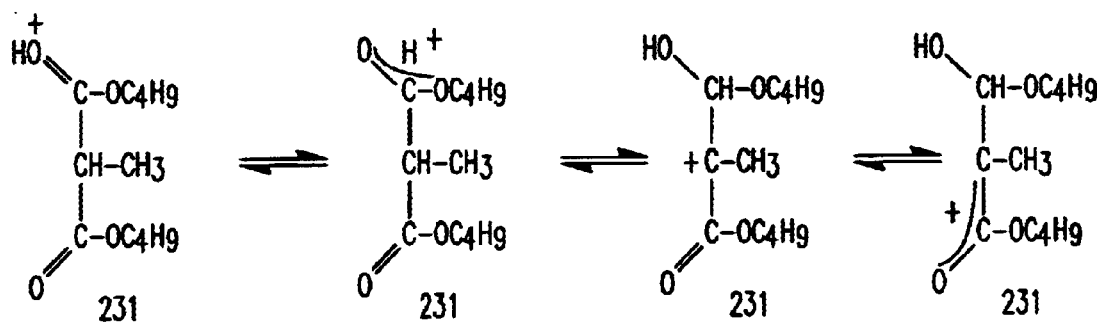
FIG. 5 illustrates the resonance structures of the protonated molecular ion of n-butyl ester of methylmalonic (A), and product ions m/z 175 (B) and m/z 119 (C)
Figure 5B:
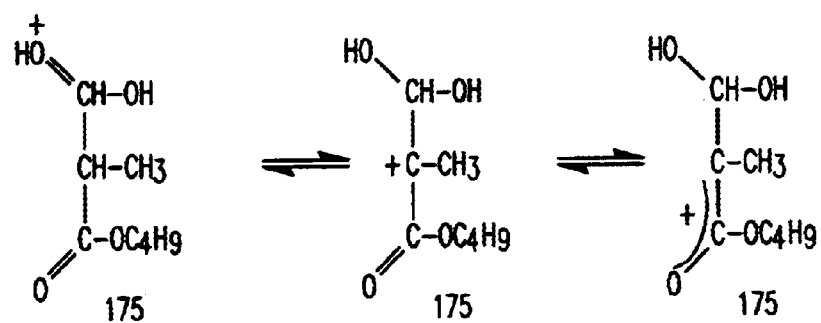
Figure 5C:
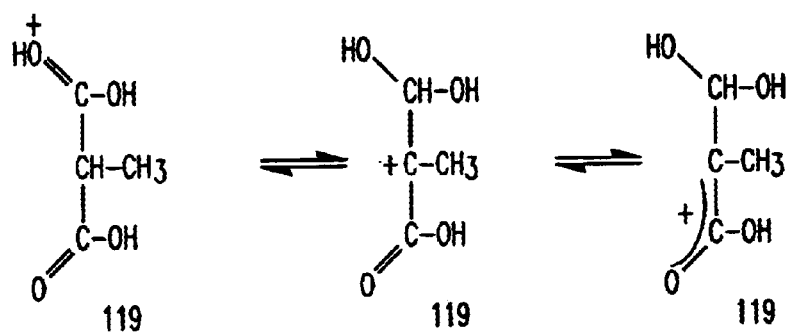

The reason for these spectral differences is believed to be the stability of the MMA m/z 119 and 175 product ions due to the potential for resonance stabilized structures and the ability to form relatively stable tertiary carbonium ions as shown by the structural schematics in FIG. 5.

Mass Spectral Data

Figure 3A:
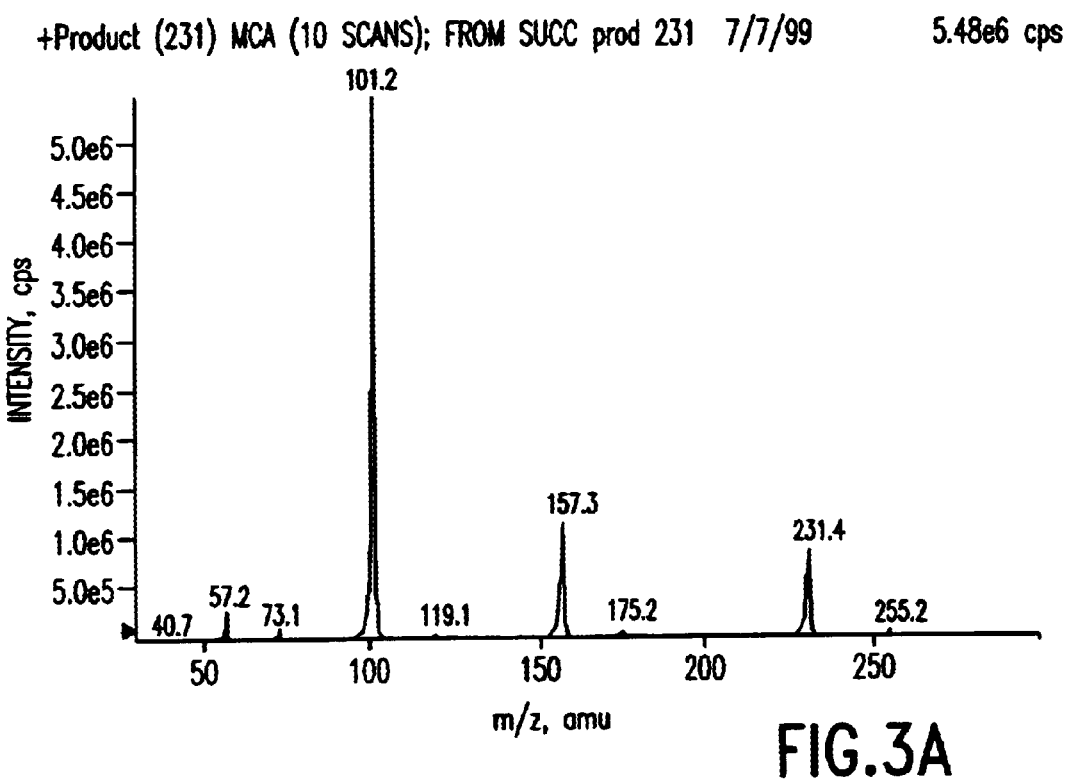
FIG. 3 is the product ion spectra of the protonated molecular ions of the dibutyl esters of succinic acid (A) and methylmalonic acid (B) in the positive ion mode.
Figure 3B:
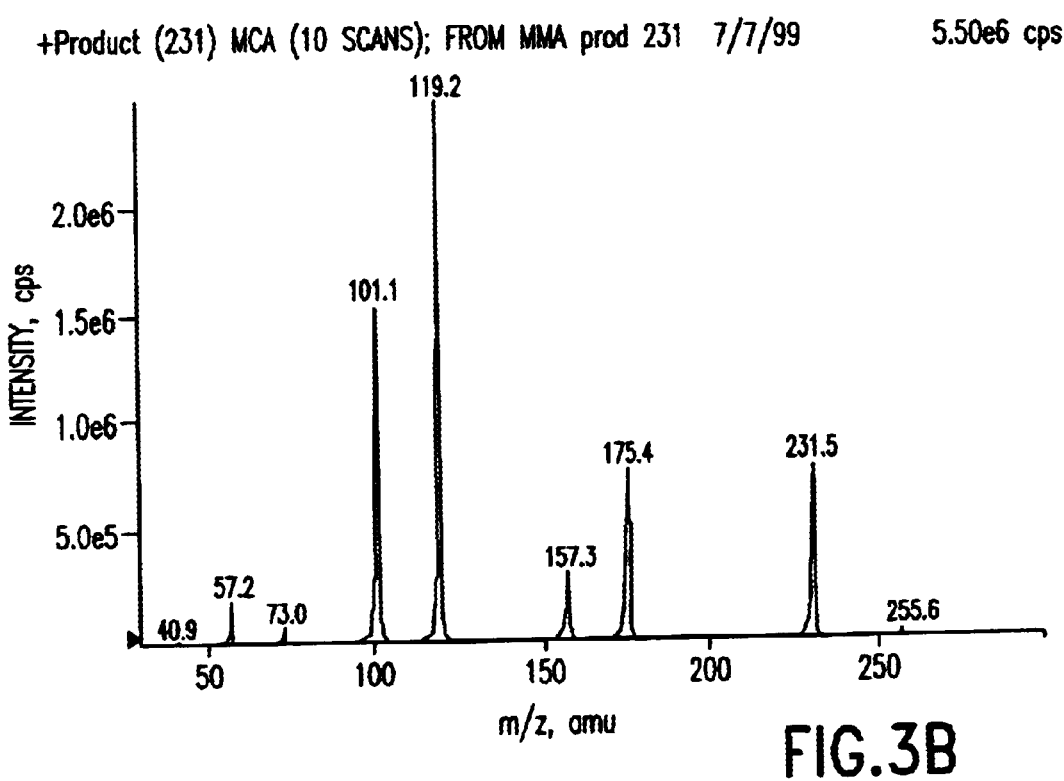
Figure 4A:
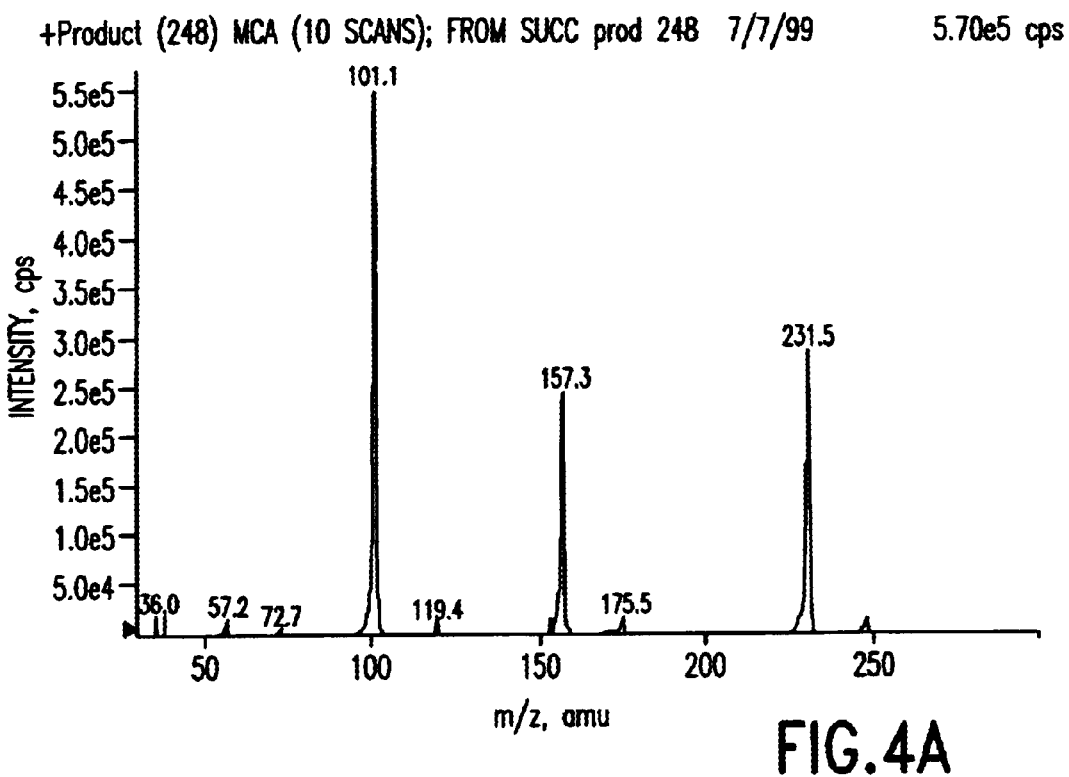
FIG. 4 is the product ion spectra of the ammoniated molecular ions of the dibutyl esters of succinic acid (A) and methylmalonic acid (B) in the positive ion mode.
Figure 4B:
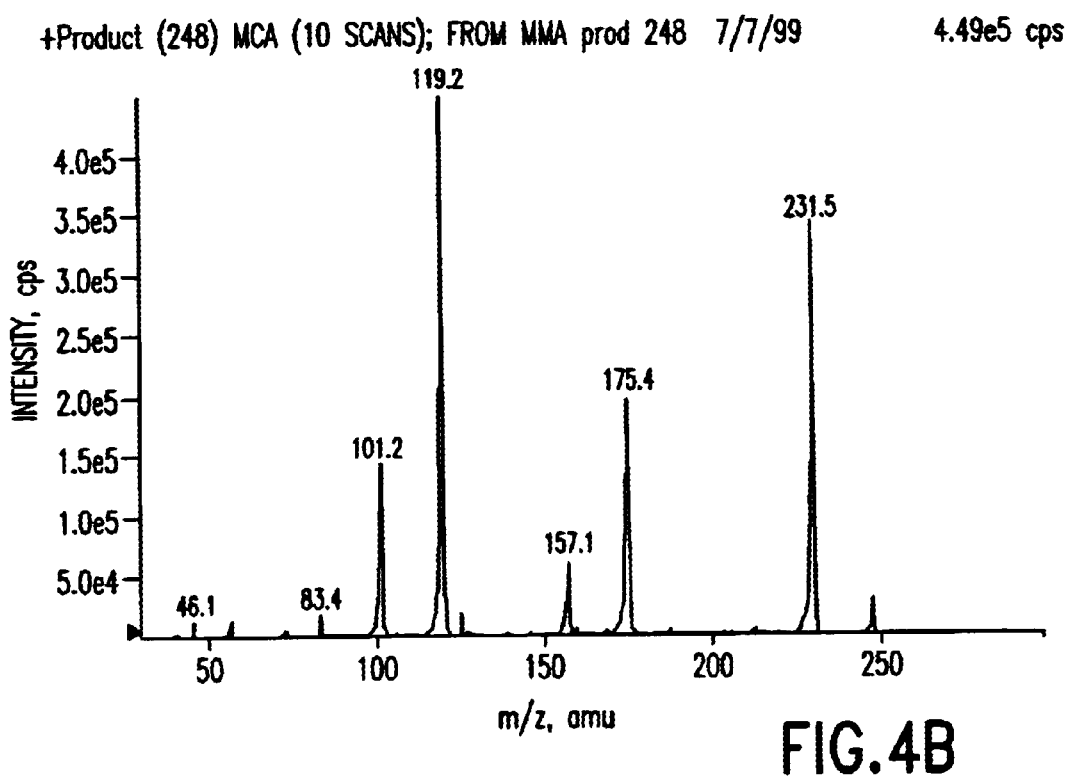

The MS—MS product ion spectrum for each of SA and MMA is provided in FIGS. 3A and 3B (full scan MS of the precursor ion m/z 231) as well as FIGS. 4A and 4B (full scan MS of the precursor ion m/z 248). Table 4 provides the relative ion intensities of product ions formed from the ammoniated (m/z 248) and protonated (m/z 231) molecular ions of succinic acid (SA) and methylmalonic acid (MMA). The data was derived from the spectra illustrated in FIGS. 3 and 4.

TABLE 4

Spectral intensities (% relative to the largest mass ion fragment) of product ions formed from the ammoniated (m/z 248) and protonated (m/z 231) molecular ions of succinic acid (SA) and methylmalonic acid (MMA)

| | m/z | 57 | 73 | 101 | 119 | 157 | 176 | 231 | Total |
|---|---|---|---|---|---|---|---|---|---|
| [M + NH$_4$]$^+$ 248 | SA | 3.0 | 1.0 | 100.0 | 2.2 | 45.6 | 3.0 | 53.5 | 208.2 |
| | MMA | 2.2 | 1.0 | 32.7 | 100.0 | 13.9 | 43.6 | 76.2 | 269.6 |
| [MH]$^+$ 231 | SA | 5.0 | 2.0 | 100.0 | ca. 1.0 | 20.8 | ca. 1.0 | 15.8 | 145.6 |
| | MMA | 7.4 | 2.5 | 61.4 | 100.0 | 11.9 | 31.2 | 31.7 | 246.1 |

Note: in all quantitative experiments, m/z 231 was used as the precursor ion for MMA

EXAMPLE 3

Comparison of Dimethylmalonic (DMMA) and Ethylmalonic (EtMA) Acids

The purpose of this comparison was to test the hypothesis that the resonance stability of the ionized MMA is due to the tertiary carbonium ion structure as illustrated in FIG. 5. The quaternary alpha-carbon of DMMA would obviate the existence of a tertiary carbonium resonance form where the trivalent carbon of EtMA would not.

The acid esters were prepared as follows. 40 uL of stock standard of each acid was aliquoted into new tubes. The solvent was evaporated and the residues reconstituted with 40 uL of 3N HCl in n-butanol. The tubes were incubated at 60° C. for 15 minutes. The excess of the derivatizing reagent was evaporated and the residues reconstituted with 4 mL of methanol containing 5% of 0.005M $NH_4$ formate. MS—MS conditions of the experiment: positive ion mode; Q1 and Q3 optimized for MMA di-n-butyl derivative; the acid's concentration was ca. 10,000 ng/mL in 95% methanol and 5% $NH_4$ formate buffer; syringe infusion flow rate 5 L/min.

IonSpray MS and MS—MS analysis of each n-butylated compound was performed. The $[MH]^+$ and $[M+NH_4]^+$ molecular ion masses (m/z) for the DMMA and EtMA derivatives are summarized in Table 4a below.

TABLE 4a

Expected molecular ion fragments for DMMA and EtMA

|  | di-n-butyl derivative | |
|---|---|---|
| Molecular ion | DMMA | EtMA |
| $[MH]^+$ | 245 | 245 |
| $[M + NH_4]^+$ | 262 | 262 |

Absolute abundance of the $[MH]^+$ and $[M+NH_4]^+$ molecular and analytically pertinent product ions of DMMA and EtMA n-butyl esters are presented in Table 4b.

TABLE 4b

| Derivative | Q1 245 $[MH]^+$ | Q1 262 $[M + NH_4]^+$ | MS-MS Ion m/z 133* product of m/z 245 |
|---|---|---|---|
| DMMA | 0.5 E6 | 0 | 1.8E5 |
| EtMA | 3.5E7 | 9E6 | 7.5E6 |

*neutral loss of 112.

There is clearly a significant difference in ionization efficiencies between DMMA and EtMA where the EtMA $[MH]^+$ signal is 70 times more intense than that of DMMA There is no detectable $[M+NH_4]^+$ signal for DMMA. This confirms the importance of the tertiary carbonium ion structure in the analysis of these dicarboxylic acids by atmospheric pressure ionization (API)-MS and MS—MS.

EXAMPLE 4

Comparison of Ionization Efficiencies and MS—MS Fragmentation for Various Alkyl-Esters of MMA and SA Relative ionization efficiencies and fragmentation patterns were evaluated for methyl, propyl, isopropyl and amyl esters of MMA and SA.

The acids esters were prepared as follows. 40 μL of stock standard of each acid was aliquoted into new tubes. The solvent was evaporated and the residues reconstituted with 100 μL of the corresponding alcohol and 50 μL of concentrated sulfuric acid. The tubes were incubated at 60° C. for 15 minutes The esters were extracted from the mix with hexane. The tubes were then centrifuged, and the organic layer transferred into new tubes. The solvent was evaporated and the residues reconstituted with 4 mL of methanol containing 5% of 0.005M $NH_4$ formate MS—MS conditions of the experiment: positive ion mode; Q1 and Q3 optimized for MMA 2-n-butyl derivative; MMA and succinic acid derivative concentrations were ca. 10,000 ng/mL in 95% methanol and 5% NH4 formate buffer; syringe infusion flow rate 5 μL/min.

$[MH]^+$ and $[M+NH_4]^+$ molecular ion fragments (m/z) for the MMA and SA derivatives are presented in the Table 7.

TABLE 7

Expected molecular ion fragments (m/z) for selected diesters of MMA and SA

| MMA and Succinic acid molecular ion | Derivative | | | | |
|---|---|---|---|---|---|
|  | Methyl | n-Propyl | Iso-propyl | n-Butyl | n-Aamyl |
| $[MH]^+$ | 147 | 203 | 203 | 231 | 259 |
| $[M + NH_4]^+$ | 164 | 220 | 220 | 248 | 276 |

Absolute abundance (cps) of the $[MH]^+$ and $[M+NH_4]^+$ mass ion fragments of MMA, SA and MS—MS transitions of $[MH]+$ to m/z 119 are presented in the Table 8.

TABLE 8

| Derivative | QI $[MH]^+$ ion abundance | | QI $[M + NH_4]^+$ ion abundance | | MS/MS Ion m/z 119 product of $[MH]^+$ | |
|---|---|---|---|---|---|---|
|  | MMA | Succinic acid | MMA | Succinic acid | MMA | Succinic acid |
| Methyl | 5.0E+05 | 4.5E+06 | 2.0E+05 | 1.0E+06 | 0.0E+00 | 0.0E+00 |
| n-Propyl | 1.0E+05 | 1.2E+07 | 1.0E+06 | 1.3E+06 | 5.5E+04 | 0.0E+00 |
| Isopropyl | 3.0E+05 | 3.2E+06 | 3.0E+05 | 2.0E+05 | 6.5E+04 | 1.4E+06 |
| n-Butyl | 7.3E+06 | 5.4E+06 | 1.3E+06 | 4.6E+06 | 3.3E+06 | 9.3E+04 |
| n-Amyl | 9.0E+06 | 2.3E+07 | 2.0E+06 | 4.0E+06 | 5.5E+06 | 7.0E+05 |

Figure 6A:
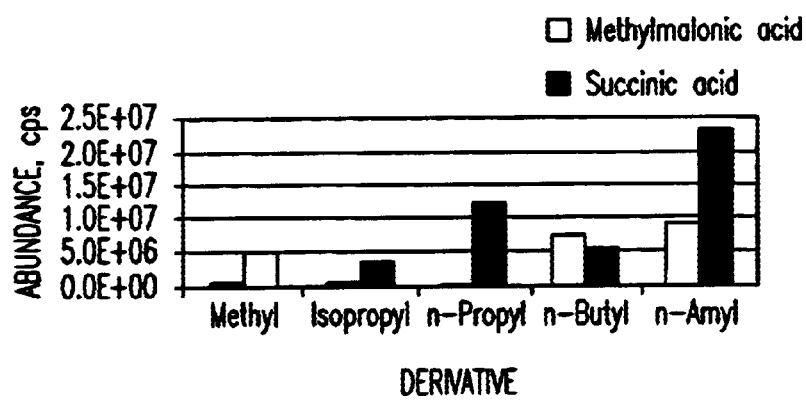
FIG. 6A is a plot of ion abundance of the $[MH]^+$ molecular ions of evaluated acid esters.
Figure 6B:
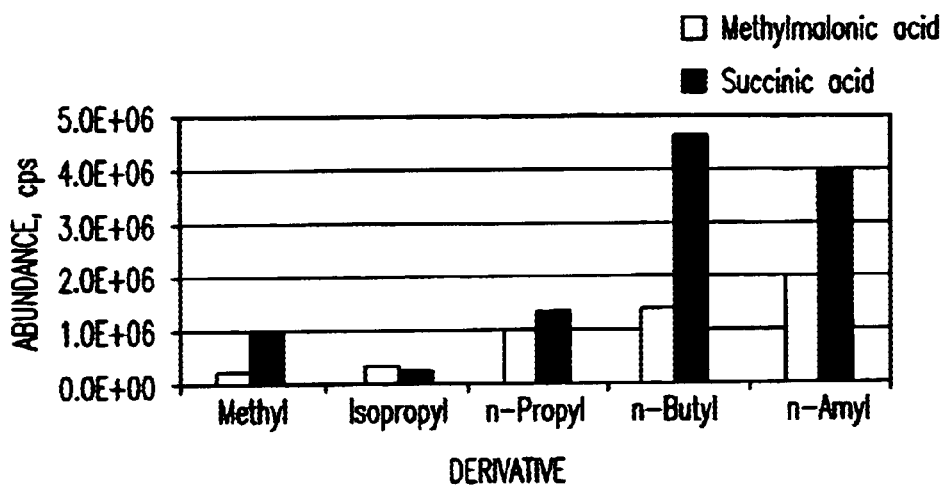
FIG. 6B is a plot of ion abundance of the $[M+NH_4]^+$ molecular ions of evaluated acid esters.
Figure 6C:
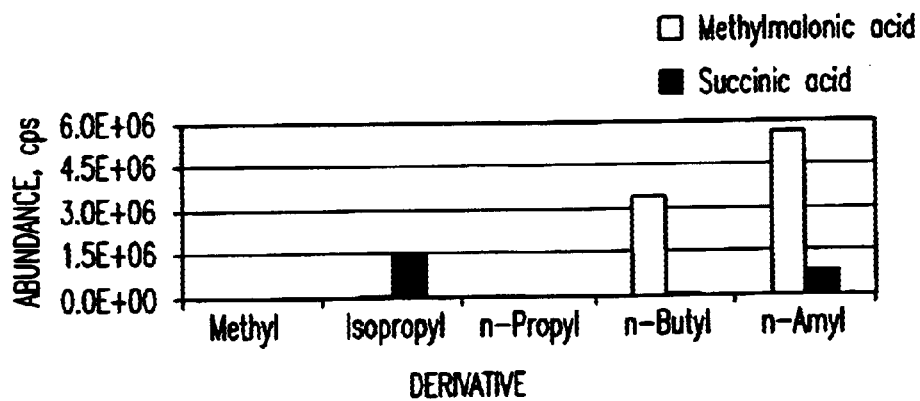
FIG. 6C is a plot of ion abundance of the m/z 119 MS—MS production.

FIGS. 6A–B are plots of the abundance of the $[MH]^+$ and $[M+NH_4]^+$ molecular ions, respectively, of the evaluated acid esters, while FIG. 6C is a plot of the abundance of the m/z 119 MS—MS product ions.

Comparison of the results in FIGS. 6A–C suggest that SA esters produce significantly more abundant [MH] molecular ions than MMA esters. The greater ion abundance could possibly be related to more stable resonance structures of the succinic acid esters, compared to the MMA esters. The results further indicate: improved ionization efficiency of derivatives with increased length of the ester alkyl chain; improved stability for $[MH]^+$ ions of MMA ester is also observed with increased length of the ester alkyl chain; the relative intensity of the $[MH]^+$ and $[M+NH_4]^+$ molecular ions varies significantly between the various esters, $[M+NH_4]^+$ ion for MMA n-propyl derivative did not lose $NH_3$ in the ion source; $[M+NH_4]^+$ ion for succinic acid n-butyl derivative was significantly more abundant than $[MH]^+$ m/z 119 product ion of $[MH]^+$ would have less cross-contribution from succinic acid compared to m/z 119 as product of [M+NH$_4$]$^+$; from the standpoint of the MMA LC-MS—MS method performance the relative ionization of the esters of MMA compared to succinic acid is the best for the n-butyl derivative; for MMA, the m/z 119 product ion cross-contribution from SA for the n-amyl derivative is 13%, compared to less than 3% for the n-butyl derivative. For specificity, the n-butyl derivative is a better choice for MMA analysis than n-amyl derivative; the n-butyl derivative has the lowest m/z 119 product ion cross-contribution with succinic acid compared to all other evaluated derivatives; isopropyl derivative would be the best choice for the analysis of succinic acid in presence of MMA; selectivity of the assays for other specified dicarboxylic acids can be realized by varying esterification reagent.

EXAMPLE 5

Analysis of Biological Samples
Method Validation:
Sample Preparation
CALIBRATION Prepare standard curve for MMA with each run in 1 mL dialyzed blank plasma as follows:

| Standard | Dialyzed plasma | Working calibration standard, µL | Working internal standard, µL |
|---|---|---|---|
| Cal. STD 0.2 µmol/L | 1 mL | 20 | 100 |
| Cal. STD 0.5 µmol/L | 1 mL | 50 | 100 |
| Cal. STD 0.75 µmol/L | 1 mL | 75 | 100 |
| Cal. STD 1.0 µmol/L | 1 mL | 100 | 100 |
| Cal. STD 1.5 µmol/L | 1 mL | 150 | 100 |
| Cal. STD 2.0 µmol/L | 1 mL | 200 | 100 |

QUALITATIVE ION RATIO STANDARD

A standard with MMA at 0.4 µmol/L and succinic acid at 6 µmol/L. Prepare by adding 8 µL of MMA stock standard (10 mmol/L) and 120 µL of succinic acid stock standard (10 mmol/L) to 200 mL of dialyzed blank plasma. Aliquot 1.2 mL of the standard into labeled microcentrifuge tubes and store at −20° C.
QUALITY CONTROL Control A, in which MMA concentration is 0.4 µmol/L is prepared by adding 8 µL of a standard containing 10 mmol/L MMA to 200 mL of dialyzed blank plasma. Control B, in which the MMA concentration is 4.0 µmol/L, is prepared by adding 80 µL of the MMA stock standard solution to 200 dialyzed blank plasma. Aliquots of 1.1–1.2 mL of each standard are transferred into labeled microcentrifuge tubes and stored at −20° C. until required.
PROCEDURE
1. Aliquot sample into a disposable glass tube.
   serum/plasma: add 1 mL of sample.
   urine: add 0.1 mL of sample and 0.9 mL of water.
2. Add 100 µL of working internal standard (15 µmol/L).
3. Add 3 mL of MTBE (Methyl-tert-butyl ether) containing 3% phosphoric acid, vortex the tubes for 5 minutes and centrifuge at 2000 g for 10 minutes.
4. Label new set of tubes with sample ID.
5. Transfer organic layer to the second set of tubes.
6. Evaporate the solvent, add 40 µL of n-butanol with 3N HCl.
7. Incubate the tubes at 50° C. for 5 minutes.
8. Evaporate excess derivatizing reagent.
9. Reconstitute the residue with 100 µL of the mobile phase.
10. Label autosampler vials and transfer tube content into the vials.

INSTRUMENTATION

Mass spectrometer API 2000 with HPLC PE series 200. The instrument utilized with TurboIonSpray interface, MRM, positive ion mode. Date analysis was performed with TurboQuan™ software.
CONDITIONS
a. LC column: Luna C8 30 mm×2 mm, 5 µm particles (Phenomenex, Calif.)
b. Mobile phase: 95% methanol, 5% of 0.005M ammonium formate buffer.
c. HPLC conditions: flow rate 0.75 ml/min, LC column effluent split flow 0.5–0.7 mL/min. Column temperature is ambient. Injection volume is 3–5 uL. Syringe wash solvent is methanol. Wash volume is 100 µL and number of syringe washes is 4.
d. MRM transitions monitored (m/z):
   MMA 231 to 119,231 to 175;
   MMA d$_3$ 234 to 122, 234 to 178. (Ions 119 and 122 are quantitative, while ions 175 and 178 are qualitative).

Qualitative ion mass ratio acceptability range is established as ±50% of the product ion fragments (m/z) (231→175)/(231→119) for MMA and (234→178)/(234→122) for MMA d$_3$ observed in the injection of the qualitative ion ratio standard.
LIMIT OF DETECTION
  0.05 µmol/L
LIMIT OF QUANTITATION
  µmol/L
UPPER LIMIT OF LINEARITY
  250 µmol/L
Precision Study:

The method precision was determined by analyzing three pools containing MMA at low, medium and high concentrations within five. High and low pools of MMA were prepared in dialyzed blood bank human plasma, spiked with MMA stock standard (10 µmol/L). The medium pool was obtained by mixing the pools in the ratio of 1:1. MMA concentration in low, medium and high pools was 0.2 µmol/L, 7.6 µmol/L and 15 µmol/L, respectively. Within-run, between-run and total precision for the results obtained in the experiments are presented in Table 9.

TABLE 9

| | Method imprecision | | |
|---|---|---|---|
| MMA, µmol/L | Within-run CV, % | Between-run/day CV,% | Total CV, % |
| 0.2 | 13.0 | 7.0 | 14.8 |
| 7.6 | 5.3 | 9.9 | 11.2 |
| 15.0 | 5.7 | 8.4 | 10.2 |

The instrument imprecision was determined by repetitive injections of a standard containing 0.4 µmol/L of MMA from the same vial. Coefficient of variation for the MMA concentration and internal standard peak area was 0.9%, and 1.8%, respectively.
Linearity Study The method linearity was evaluated by analyzing standards prepared at 1, 51, 101, 125.5, 150, 200, and 250 µmol/L. The standards were prepared from two dialyzed plasma pools of 1 µmol/L and 250 µmol/L. The other standards were prepared by spiking the pools in ratios 4:1, 3:2, 1:1, 2:3, 1:4, respectively. Each standard was analyzed in duplicate and concentrations were calculated from the standard curve obtained with the standards containing 0.2, 0.5, 0.75, 1.0, 1.5, 2.0 µmol/L of MMA. Utilizing a criterion of maintaining accuracy of ±20% of a target value the assay was found to be linear up to 250 µmol/L, with accuracy declined 7% at the highest evaluated concentration of 250 µmol/L. Concentrations quantitated above 250 µmol/L should be reported as above 260 µmol/L.

Sensitivity Study

Method sensitivity was determined by analyzing standards containing progressively lower concentration of MMA with criteria of maintaining accuracy within ±20%. In two separate studies, the 0.1 µmol/L standard averaged 0.11 µmol/L with accuracy of 113% and imprecision 18%. Limit of quantitation for the method is 0.1 µmol/L and equals 50% of the low calibrator. Limit of detection (LOD) for the method was determined as the lowest concentration that produced a peak with ion ratio consistent with values established by calibration and peak size 10 times greater than the background noise, The LOD was determined to be 0.05 µmol/L. Concentrations quantitated below 0.1 µmol/L should be reported as less than 0.1 µmol/L.

Figure 7A:
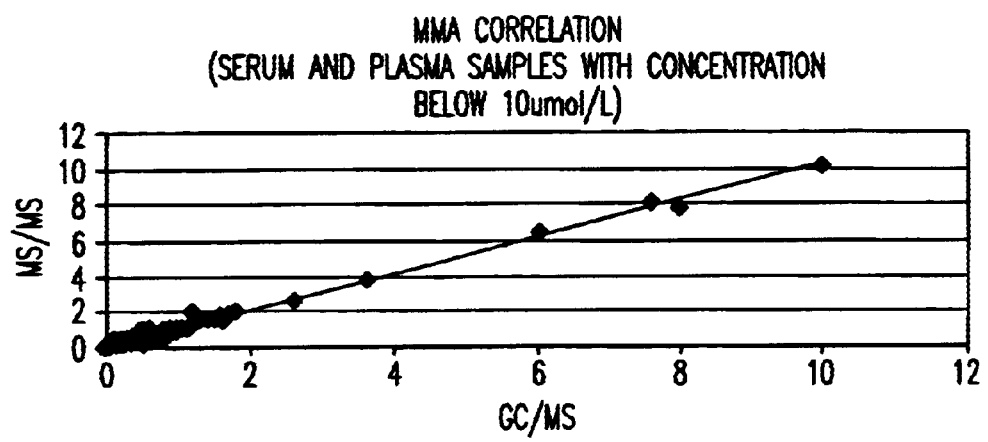
FIG. 7A is the correlation of LC-MS—MS results for MMA in serum and plasma versus GC/MS for the concentration range 0 to 10 μmol/L.

Accuracy Study 256 samples were included in the correlation study (178 serum and plasma patient samples, 13 urine patient samples and 65 samples spiked in dialyzed plasma). All the patient samples included in the study were previously analyzed by the in-house GC/MS assay [30]. Among the spiked samples included in the study 32 were controls utilized with every run, and the remaining 33 spiked samples were utilized because the number of patient samples with concentration above 10 µmol/L was not sufficient for the correlation. The samples were analyzed within 12 days with 7 to 34 specimens per run. The results were grouped in three sets according to the concentration and the sample matrix (serum/plasma or urine). The first group contained serum/plasma samples with concentrations from 0.1 to 10 µmol/L (FIG. 7A). The second group contained results obtained by analysis of all the available serum/plasma samples, and the third group included results for the urine samples. To account for bias in both the reference and the evaluated methods, the results were analyzed by Deming regression [46]. The correlation coefficient and standard error for the comparison within the range of 0.1 to 10 µmol/L (serum/plasma) were 0.992 and 0.1 µmol/L, respectively.

Figure 7B:
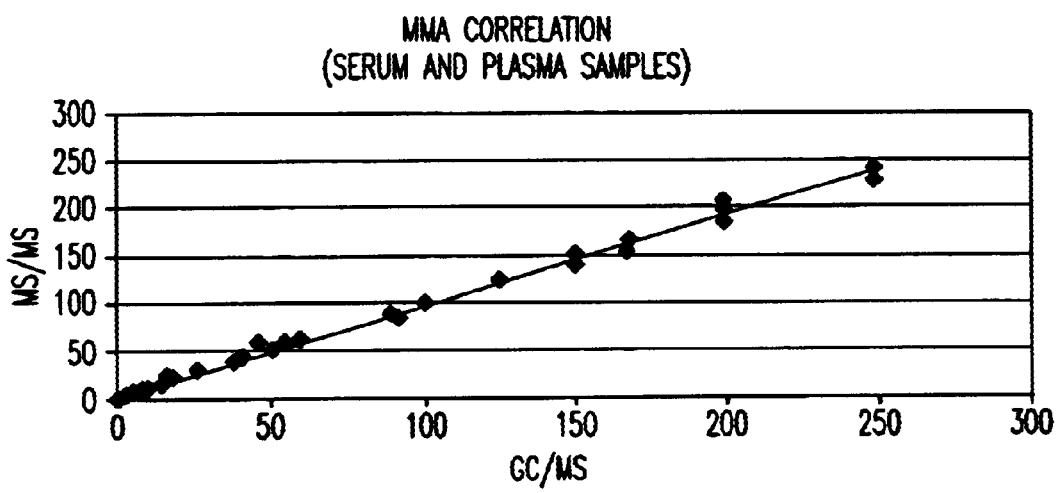
FIG. 7B is the correlation of LC-MS—MS results for MMA in serum and plasma versus GC/MS for the concentration range 0 to 250 μmol/L.

The correlation coefficient and standard error values for the serum and plasma samples with concentration within the range of 0.1 to 250 µmol/L were 0.996 and 2.2 µmol/L, respectively (FIG. 7B).

The linear regression equations for the correlation were y=1.016* x+0.05 for the range of 0.1 to 10 µmol/L, and y=0.950* x+0.51 for the range of 0.1 to 250 µmol/L, respectively.

Figure 8:
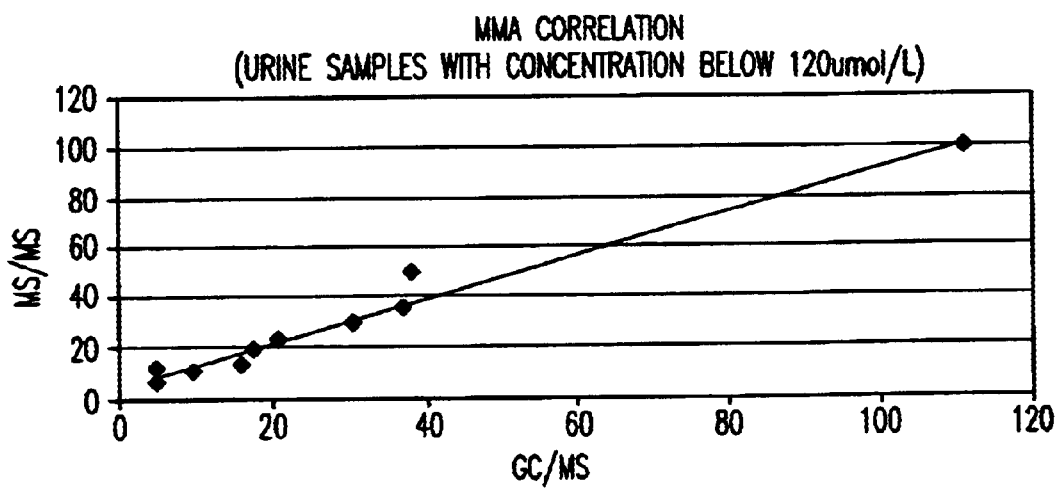
FIG. 8 is the correlation of LC-MS—MS results for MMA in urine versus GC/MS for the concentration range 0 to ca. 120 μmol/L.

The correlation coefficient, standard error and regression equation for the comparison for the analyzed urine samples within the range of 10 to 120 µmol/L were 0.971, 3.4 µmol/L, and y=0.903* x+2.32 respectively (FIG. 8). (Results for the sample not included in the plot were 5908 µmol/L by the GC/MS assay and 5683 µmol/L by the present method). The data indicated that no significant bias existed between the methods.

Interference Study 22 mixtures of organic acid standards were prepared with 3–5 standards in each mixture. The total number of acids included in the study was 77, with a concentration of each individual acid in the mixture of 10,000 µmol/L. Acids included in the study are presented in Table 10. The n-butyl esters of the acids were prepared as described in Example 1.

TABLE 10

Organic acids evaluated for potential interference with MMA analysis.

| | |
|---|---|
| 1,12-Dodecanedioic acid | 2-Hydroxyisobutyric acid |
| 2-Hydroxy-3-methylvaleric acid | 2-Hydroxyisovaleric acid |

TABLE 10-continued

Organic acids evaluated for potential interference with MMA analysis.

| | |
|---|---|
| 2-Hydroxybutyric acid | 2-Hydroxyphenylacetic acid |
| 2-Hydroxyglutaric acid | 2-Ketoadipic acid |
| 2-Methyladipic acid | Levulinic acid |
| 2-Oxoglutaric acid | Linoleic acid |
| 2-Oxohexanoic acid | Linolenic acid |
| 2-Oxoisocaproic acid | m-Hydroxyphenylacetic acid |
| 2-Oxoisovaleric acid | Malic acid |
| 3-Hydroxy-3-methylglutaric acid | Malonic acid |
| 3-Hydroxybutyric acid | Methylcitric acid |
| 3-Hydroxyisobutyric acid | Methylsuccinic acid |
| 3-Methyl-2-oxovaleric acid | N-Acetylaspartic acid |
| 3-Methyladipic acid | N-Acetyltyrosine |
| 3-Methylglutaric acid | o-Hydroxyphenylacetic acid |
| 4-Hydroxyphenylacetic acid | Oleic acid |
| 4-Hydroxyphenylpyruvic acid | Orotic acid |
| 5-Hydroxyindolacetic acid | Oxalic acid |
| Acetoacetic acid | p-Hydroxybenzoic acid |
| (trans-)Aconitic acid | Palmitic acid |
| Adipic acid | Palmitoleic acid |
| Azelaic acid | Phenylacetic acid |
| Benzoic acid | Phenyllactic acid |
| Caproic acid | Phenylpyruvic acid |
| Caprylic acid | Pimelic acid |
| Citric acid | Propionic acid |
| Ethylmalonic acid | Pyroglutamic acid |
| Fumaric acid | Pyruvic acid |
| Glutaric acid | Sebacic acid |
| Glyceric acid | Stearic acid |
| Glycerol | Suberic acid |
| Glycolic acid | Succinic acid |
| Glyoxylic acid | Succinylacetone |
| Hippuric acid | Tetradecanedioic acid |
| Homogentistic acid | Tropic acid |
| Homovanillic acid | Vanillylmandelic acid |
| Isocitric acid | |
| Lactic acid | |
| Lauric acid | |

The samples were analyzed by the present MMA method in MRM and product ion scan modes. Acids from the samples with suspected interference were analyzed separately in the following run. The only acids potentially causing interference with MMA analysis were succinic, sebacic and succinylacetone. Succinic acid present at a concentration of 20 µmol/L produced a signal equivalent to <0.4 µmol/L of MMA with a significantly elevated qualitative ion ratio (>2 when 0.5 is expected for MMA). Sebacic acid and succinylacetone, when present at a concentration of 1000 µmol/L, produced signals equivalent to 0.01 and 0.1 µmol/L of MMA, respectively. The qualitative ion ratio for both these compounds was also outside of the acceptable range, i.e. 0.5±0.25.

If an unidentified interference is present in a specimen, the sample should be reinjected. If the interference is not resolved, the sample should be re-analyzed by a method chromatographically resolving MMA and SA, or a new sample should be requested.

Sample Collection

Among the samples included in the correlation study were some that were hemolyzed and lipimic. These samples worked without noticeable difference from the others. Commonly utilized serum collection tubes were evaluated for acceptability of serum sample collection. Out of the evaluated EDTA, heparin, oxalate and citrate collection tubes, some interference was observed only for the citrate tube. Citrate itself did not interfere with MMA quantitation, but the matrix within the tube did interfere and produced a significant elevation for the qualitative ion ratio of MMA.

Carryover Study

An experiment was performed to evaluate the syringe wash and LC system for MMA carryover from a specimen containing an extremely elevated concentration of MMA to the following sample. The carryover potential was evaluated by injecting a negative control after a sample containing 1000 µmol/L of MMA. No carryover to the following sample and to the following injection was detected (carryover to the negative control was less than the LOD of the method). The wash protocol for the autosampler syringe was set to 4 washes with methanol after every injection.

Sample Stability Study

Samples may be frozen at −20° C. or less for up to 6 months, or refrigerated for up to one week prior to analysis.

IonSpray vs. Heated Nebulizer-APCI

The two ionization methods were evaluated and there was no appreciable difference to the present method. Either APCI/Heated Nebulizer or IonSpray (electrospray) could be used. The sensitivity for MMA was diminished by about a factor of 5 using the Heated Nebulizer inlet.

REFERENCES

1. Cox E V, White A M. Lancet 1962; 853–456.
2. Burtis C A, Ashwood E R. Teits textbook of clinical chemistry W. B. Saunders Company, Philadelphia, 1994, pp 2048–2049.
2a. Stabler S P, Marcell P D, Podell E R and Allen R H; Lindenbaum J, J Clin Invest, 77(5):1606–12 1986 May.
3. Fenton W A, Rosenberg L E. Disorders of Propionate and Methylmalonate Metabolism, in The Metabolic and Molecular Bases of Inherited Disease, (Scriver C R, Beaudet A L, Sly W S, Valle D eds.), McGraw-Hill, Inc. New York, 1995, pp. 1423–1449.
4. Barness L A, Young D, Mellman W J, Kahn S B, Williams W J. N Engl J Med 1963; 268(3):144–146.
5. Giorgio A J, Plaut G W E. J Lab Clin Med 1965; 66(4):667–676.
6. Bashir H V, Hinterberger H, Jones B P. Br J Haemafol 1966; 12:704–711.
7. Westwood A, Taylor W, Davies G. Ann Clin Biochem 1979; 16:161–164.
8. Coulombe J T, Shih V E, Levy H L. Pediatrics 1981; 67:23–31.
9. Schneede J, Ueland P M. Clin Chem 1993; 39:392–399.
10. Babidge P J, Babidge W J. Anal Biochem 1994; 216; 424–426.
11. Schneede J, Ueland P M. Anal Chem 1995; 67:812–819.
12. Gibbs B F, Itiaba K, Mamer O A, Crawhall J C, Cooper B A. Clin Chim Acta 1972; 38:447–453.
13. Lorentz P P, Gibb F M. Lab Pract 1974; 23:438.
14. Nakamura E, Rosenberg L E, Tanaka K. Clin Chim Acta 1976; 68:127–1401.
15. Norman E J, Berry H K, Denton M D. Biomed Mass Spectrom 1979; 6:546–552.
16. Norman E J, Martelo O J, Denton M D. Blood 1982; 59:1128–1131.
17. Jakobs C, Sweetman L, Nyhan W L. Clin Chim Acta 1984; 140:157–166.
18. Marcell P D, Stabler S P, Podell E R, Allen R H. Anal Biochem 1985; 150:58–66.
19. Stabler S P, Marcell P D, Podell E R, Allen R H, Lindenbaum J. J Clin Invest 1986; 77:1606–1612.
20. Matchar D B, Feussner J R, Millington D S, Wilkinson R H, Watson D J, Gale I D. Ann Int Med 1987; 106:707–710.
21. Montgomery J A, Mamer O A. Methods Enzymol 1988; 166:47–55.
22. Rasmussen K Clin Chem 1989; 35:260–264.
23. McGhie T K. J Cromatogr 1991; 566:215–222.
24. Straczek J, Felden F, Dousset B, Gueant J L, Belleville F. J Chromatogr Blamed Appl 1993; 620:1–7.
25. Young P B, Blanchflower W J, Hewitt S A, Price J, Kennedy D G. Analyst 1995; 120:2199–2201.
26. McCann M T, Thompson M M, Gueron I C, Lemieux B, Giguere R, Tuchman M. Clin Chem 1996; 42:910–914.
27. Parnet J M, Divry P, Vianey-Saban C, Mathieu M. J Inher Metab Dis 1996; 19:635–637.
28. Johnson A W, Mills K, Clayton P T. Biochem Soc Trans 1996; 24:932–938.
29. Rifai N, Hagen T, Bradley L, Sakamoto M. Ann Clin Biochem 1998; 35:633–636.
30. Kushnir M M, Komaromy-Hiller G. J ChromatogrB, 2000;741:231–41.
31. Mills G A, Walker V, Clench M R, Parr V C. Biomed Environ Mass Spectrom 1988;16–259–261.
32. Buchanan D N, Muenzer J, Thoene J G. J Chromatogr 1990; 534:1–11.
33. Millar K R, Lorentz P. P J Chromatogr 1974; 101:177–181.
34. Frenkel E P, Kitchens R L. J Clin Lab Med 1975; 85:487–496.
35. Mikasa H, Sasaki K, Kodama H. J Chromatogr 1980; 190:501–503.
36. Rinaldo P, Chiandetti L, Zacohello F, Daolio S, Traldi P. Biomed Mass Spectrom 1984; 11:643–646.
37. Kajita M, Niwa T, Watanabe K. J Chromatogr Biomed Appl 1993; 622:263–268.
38. Marsh D S B, Nuttall K L. J Cap Elec 1995; 2:63–67.
39. Franke D R, Marsh D B, Nuttall K L. J Cap Elec 1996; 3:125–129.
40. Allen R H, Stabler S P, Lindenbaum J, U.S. Pat. No. 4,940,658, Jul. 10, 1990.
41. Johnson D W, Rapid Commun. Mass Spectrom., 1999, 13:1–6.
42. Chace D H, Millington D S, Terada N, Kahler S G, Roe C R, Hofman L F, Clin Chem 1993 39; 66–71.
43. Rashed M S, Ozand P T, Bucknall M P, and Little, D, Pediatr. Res, 1995 38; 324–331.
44. Bruins, et. al. 1999.
45. T. Niwa J. Chromatogr 1986; 379:313–45.
46. J. Cornbleet, N. Gochman, Clin. Chem., 25 (1979) 432.

We claim:

1. A method for selectively analyzing at least one dicarboxylic acid in a sample comprising the steps of:
   1) extracting the acidic component from the sample;
   2) derivatizing the acidic component to form saturated or unsaturated alkyl di-esters; and
   3) analyzing the derivatized acidic component using mass spectrometry and atmospheric pressure ionization in the positive ion mode to analyze a dicarboxylic acid of interest, wherein the alkyl ester of said dicarboxylic acid yields a stable protonated molecular ion on ionization.

2. A method as defined in claim 1, wherein the alkyl esters are n-butyl esters.

3. A method as defined in claim 2, wherein the dicarboxylic acid is methylmalonic acid.

4. A method as defined in claim 3, wherein the n-butyl ester of methylmalonic acid is characterized as a positively charged adduct precursor.

5. A method as defined in claim 4, wherein the n-butyl ester of methylmalonic acid is characterized as a protonated precursor molecular ion of mass-to-charge (m/z) 231, and fragment ions of mass-to-charge (m/z) 119 and 175 using tandem mass spectrometry.

6. A method as defined in claim 4, wherein the n-butyl ester of methylmalonic acid is characterized as an ammoniated precursor molecular ion of mass-to-charge (m/z) 248, and fragment ions of mass-to-charge (m/z) 119 and 175 using tandem mass spectrometry.

7. A method as defined in claim 1, wherein the mass spectrometry is tandem mass spectrometry.

8. A method as defined in claim 1, wherein the atmospheric pressure ionization is selected from the group consisting of electrospray, nebulizer assisted electrospray, APCI-heated nebulizer or atmospheric pressure photoionization (APPI) in the positive ion mode.

9. A method as defined in claim 1, wherein the acidic component is extracted by liquid—liquid or solid phase extraction.

10. A method as defined in claim 9, wherein the acidic component is extracted with methyl tert-butyl ether in the presence of phosphoric acid.

11. A method as defined in claim 1, wherein the esterified sample is subjected to a filtration step.

12. A method as defined in claim 11, wherein the filtration is achieved by liquid chromatography.

13. A method as defined in claim 1, including the additional step of determining the concentration of the dicarboxylic acid of interest based on the response of the mass spectrometer.

14. A method as defined in claim 13, wherein the concentration of dicarboxylic acid is determined using an internal standard.

15. A method as defined in claim 14, wherein the internal standard is deuterated methylmalonic acid.

16. A method as defined in claim 15, wherein the concentration of methylmalonic acid is determined based on the ratio of the MS—MS transition (m/z) 231→119 to the corresponding MS—MS transition of a deuterated MMA internal standard and the presence of methylmalonic acid is confirmed based on the ratio of the M$-MS transitions (m/z) 231→175 to 231→119.

17. A method for determining the presence of methylmalonic acid in a sample comprising the steps of:

1) extracting the acidic component of the sample;

2) derivatizing the acidic component to form n-butyl esters; and 3) analyzing the derivatized acidic component to determine the presence of methylmalonic acid in the sample using tandem mass spectrometry and atmospheric pressure ionization in the positive ion mode.

18. A method as defined in claim 17, wherein the n-butyl ester of methylmalonic acid is characterized as a protonated precursor molecular ion of mass-to-charge (m/z) 231, and fragment ions of mass-to-charge (m/z) 119 and 175 using tandem mass spectrometry.

19. A method as defined in claim 17, wherein the n-butyl ester of methylmalonic acid is characterized as an ammoniated precursor molecular ion of mass-to-charge (m/z) 248, and fragment ions of mass-to-charge (m/z) 119 and 175 using tandem mass spectrometry.

20. A method as defined in claim 17, including the additional step of determining the concentration of the methylmalonic acid in the sample based on the response of the tandem mass spectrometer.

21. A method as defined in claim 20, wherein the concentration of methylmalonic acid is determined based on the ratio of the MS—MS transition (m/z) 231→119 to the corresponding MS—MS transition of a deuterated MMA internal standard and the presence of methylmalonic acid is confirmed based on the ratio of MS—MS transitions 231→175 to 231→119.

22. A method for diagnosing vitamin $B_{12}$ deficiency in a patient comprising the steps of:

1) obtaining a biological sample from the patient;

2) extracting the acidic component from the sample;

3) derivatizing the acidic component to form saturated or unsaturated alkyl esters;

4) analyzing the derivatized acidic component of the sample by tandem mass spectrometry employing atmospheric pressure ionization in the positive ion mode; and 5) determining the presence of methylmalonic acid at a concentration of at least 0.4 µmol/L in the sample.

23. A method as defined in claim 22, wherein the acidic component is derivatized to form n-butyl esters.

24. A method as defined in claim 23, wherein the n-butyl ester of methylmalonic acid is characterized as a protonated precursor molecular ion of m/z 231, and fragment ions of m/z 175 and 119 using tandem mass spectrometry.

25. A method as defined in claim 23, wherein the n-butyl ester of methylmalonic acid is characterized as an ammoniated precursor molecular ion of mass-to-charge (m/z) 248, and fragment ions of mass-to-charge (m/z) 119 and 175 using tandem mass spectrometry.

26. A method as defined in claim 22, wherein the concentration of methylmalonic acid is determined based on the MS—MS transition (m/z) 231→119 and the presence of methylmalonic acid is determined based on the ratio of the MS—MS transition (m/z) 231→175 to 231→119.

27. A method as defined in claim 22, wherein the concentration of methylmalonic acid is determined using an internal standard.

28. A method as defined in claim 27, wherein the internal standard is deuterated methylmalonic acid.

29. A method as defined in claim 27, wherein the lack of interference with the internal standard is confirmed based on the ratio of the MS—MS transitions (m/z) 234→178 to 234→122.

* * * * *